United States Patent
Jackson

(10) Patent No.: US 10,779,864 B2
(45) Date of Patent: Sep. 22, 2020

(54) PIVOTAL BONE ANCHOR ASSEMBLY WITH RECEIVING AND LOCKING MEMBERS ENGAGEABLE BY INDEPENDENT LOCK AND RELEASE TOOLING

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 16/707,900

(22) Filed: Dec. 9, 2019

(65) Prior Publication Data

US 2020/0107863 A1 Apr. 9, 2020

Related U.S. Application Data

(63) Continuation of application No. 16/518,047, filed on Jul. 22, 2019, now Pat. No. 10,499,958, which is a continuation of application No. 16/418,778, filed on May 21, 2019, now abandoned, which is a continuation of application No. 16/371,423, filed on Apr. 1, 2019, which is a continuation of application No. 15/885,443, filed on Jan. 31, 2018, now Pat. No. 10,245,078, which is a continuation of application No. 15/703,567, filed on Sep. 13, 2017, now Pat. No. 10,278,739, which is a continuation of application (Continued)

(51) Int. Cl.
| | |
|---|---|
| *A61B 17/70* | (2006.01) |
| *A61B 17/86* | (2006.01) |
| *A61B 90/00* | (2016.01) |
| *F16B 35/00* | (2006.01) |

(52) U.S. Cl.
CPC .......... *A61B 17/7037* (2013.01); *A61B 17/70* (2013.01); *A61B 17/7001* (2013.01); *A61B 17/7002* (2013.01); *A61B 17/704* (2013.01); *A61B 17/7032* (2013.01); *A61B 17/7035* (2013.01); *A61B 17/7082* (2013.01); *A61B 17/7091* (2013.01); *A61B 17/8605* (2013.01); *A61B 2090/037* (2016.02); *F16B 35/005* (2013.01)

(58) Field of Classification Search
CPC .................. A61B 17/7035; A61B 17/7032
See application file for complete search history.

(56) References Cited

U.S. PATENT DOCUMENTS

| | | |
|---|---|---|
| 4,805,602 A | 2/1989 | Puno et al. |
| 4,946,458 A | 8/1990 | Harms et al. |

(Continued)

*Primary Examiner* — Andrew Yang
(74) *Attorney, Agent, or Firm* — Polsinelli PC

(57) ABSTRACT

A pivotal bone anchor assembly configured for independent positional locking with tooling prior to securing an elongate rod to patient bone with a closure. The assembly includes a bone anchor having a capture portion and a body portion for fixation to patient bone. The assembly also includes a receiving member having an upper portion for receiving the elongate rod and a lower portion for receiving the capture portion, with the bone anchor having pivotal movement with respect to the receiving member. The assembly further includes a locking member in non-threaded engagement with the receiving member and configured for vertical displacement by the tooling into a locked configuration, so as to lock an angular position of the bone anchor relative to the receiving member. The locking member is also releasable by the tooling to re-establish the pivotal movement of the bone anchor with respect to the receiving member.

22 Claims, 23 Drawing Sheets

Related U.S. Application Data

No. 15/702,442, filed on Sep. 12, 2017, now Pat. No. 10,064,660, which is a continuation of application No. 15/401,618, filed on Jan. 9, 2017, now Pat. No. 9,788,866, which is a continuation of application No. 15/094,870, filed on Apr. 8, 2016, now Pat. No. 9,801,665, which is a continuation of application No. 14/026,150, filed on Sep. 13, 2013, now Pat. No. 9,308,027, which is a continuation of application No. 12/802,668, filed on Jun. 11, 2010, now Pat. No. 9,456,853, which is a continuation of application No. 11/140,343, filed on May 27, 2005, now Pat. No. 7,776,067.

(56) References Cited

U.S. PATENT DOCUMENTS

| | | |
|---|---|---|
| 5,129,388 A | 7/1992 | Vignaud et al. |
| 5,167,664 A | 12/1992 | Hodorek |
| 5,207,678 A | 5/1993 | Harms et al. |
| 5,261,912 A | 11/1993 | Frigg |
| 5,312,404 A | 5/1994 | Asher et al. |
| 5,360,431 A | 11/1994 | Puno et al. |
| 5,395,371 A | 3/1995 | Miller et al. |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,496,321 A | 3/1996 | Puno et al. |
| 5,554,157 A | 9/1996 | Errico et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,426 A | 3/1997 | Ralph et al. |
| 5,624,442 A | 4/1997 | Mellinger et al. |
| 5,669,911 A | 9/1997 | Errico et al. |
| 5,672,176 A | 9/1997 | Biedermann et al. |
| 5,681,319 A | 10/1997 | Biedermann et al. |
| 5,690,630 A | 11/1997 | Errico et al. |
| 5,716,356 A | 2/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,954,725 A | 9/1999 | Sherman et al. |
| 5,961,517 A | 10/1999 | Biedermann et al. |
| 5,964,760 A | 10/1999 | Richelsoph |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,187,005 B1 | 2/2001 | Brace et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,302,888 B1 | 10/2001 | Mellinger et al. |
| 6,309,391 B1 | 10/2001 | Crandall et al. |
| 6,355,040 B1 | 3/2002 | Richelsoph et al. |
| RE37,665 E | 4/2002 | Ralph et al. |
| 6,368,321 B1 | 4/2002 | Jackson |
| 6,440,137 B1 | 8/2002 | Horvath et al. |
| 6,443,953 B1 | 9/2002 | Perra et al. |
| 6,471,705 B1 | 10/2002 | Biedermann et al. |
| 6,485,494 B1 | 11/2002 | Haider |
| 6,488,681 B2 | 12/2002 | Martin et al. |
| 6,520,963 B1 | 2/2003 | McKinley |
| 6,530,929 B1 | 3/2003 | Justis et al. |
| 6,540,749 B2 | 4/2003 | Schafer et al. |
| 6,554,834 B1 | 4/2003 | Crozet et al. |
| 6,565,565 B1 | 5/2003 | Yuan et al. |
| 6,565,567 B1 | 5/2003 | Haider |
| 6,626,908 B2 | 9/2003 | Cooper et al. |
| 6,652,526 B1 | 11/2003 | Arafiles |
| 6,660,004 B2 | 12/2003 | Barker et al. |
| 6,695,843 B2 | 2/2004 | Biedermann et al. |
| 6,716,214 B1 | 4/2004 | Jackson |
| 6,723,100 B2 | 4/2004 | Biederman et al. |
| 6,755,829 B1 | 6/2004 | Bono et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 7,066,937 B2 | 6/2006 | Shluzas |
| 7,087,057 B2 | 8/2006 | Konieczynski et al. |
| 7,144,396 B2 | 12/2006 | Shluzas |
| 7,160,300 B2 | 1/2007 | Jackson |
| 7,179,261 B2 | 2/2007 | Sicvol et al. |
| 7,306,606 B2 | 12/2007 | Sasing |
| 7,377,923 B2 | 5/2008 | Purcell et al. |
| 7,491,218 B2 | 2/2009 | Landry et al. |
| 7,503,924 B2 | 3/2009 | Lee |
| 7,527,638 B2 | 5/2009 | Anderson et al. |
| 7,618,444 B2 | 11/2009 | Shluzas |
| 7,678,137 B2 | 3/2010 | Butler et al. |
| 7,717,939 B2 | 5/2010 | Ludwig et al. |
| 7,811,310 B2 | 10/2010 | Baker et al. |
| 7,951,172 B2 | 5/2011 | Chao et al. |
| 8,021,397 B2 | 9/2011 | Farris et al. |
| 9,456,853 B2 | 10/2016 | Jackson |
| 9,788,866 B2 | 10/2017 | Jackson |
| 9,801,665 B2 | 10/2017 | Jackson |
| 9,999,452 B2 | 6/2018 | Jackson |
| 10,039,577 B2 | 8/2018 | Jackson |
| 10,064,660 B2 | 9/2018 | Jackson |
| 10,245,078 B2 | 4/2019 | Jackson |
| 10,278,739 B2 | 5/2019 | Jackson |
| 2001/0001119 A1 | 5/2001 | Lombardo |
| 2002/0133154 A1 | 9/2002 | Saint Martin |
| 2003/0100896 A1 | 5/2003 | Biedermann et al. |
| 2003/0149431 A1 | 8/2003 | Varieur |
| 2003/0187433 A1 | 10/2003 | Lin |
| 2004/0153068 A1 | 8/2004 | Janowski et al. |
| 2004/0193160 A1 | 9/2004 | Richelsoph |
| 2004/0225289 A1 | 11/2004 | Biedermann et al. |
| 2005/0049589 A1 | 3/2005 | Jackson |
| 2005/0192570 A1 | 9/2005 | Jackson |
| 2005/0192573 A1 | 9/2005 | Abdelgany et al. |
| 2005/0216000 A1 | 9/2005 | Colleran |
| 2006/0111713 A1 | 5/2006 | Jackson |
| 2006/0129149 A1 | 6/2006 | Iott et al. |

(56) References Cited

U.S. PATENT DOCUMENTS

| | | |
|---|---|---|
| 2006/0217716 A1 | 9/2006 | Baker et al. |
| 2015/0142060 A1 | 5/2015 | Jackson |
| 2016/0015433 A1 | 1/2016 | Jackson |
| 2017/0181775 A1 | 6/2017 | Jackson |
| 2019/0223918 A1 | 7/2019 | Jackson |
| 2019/0269439 A1 | 9/2019 | Jackson |

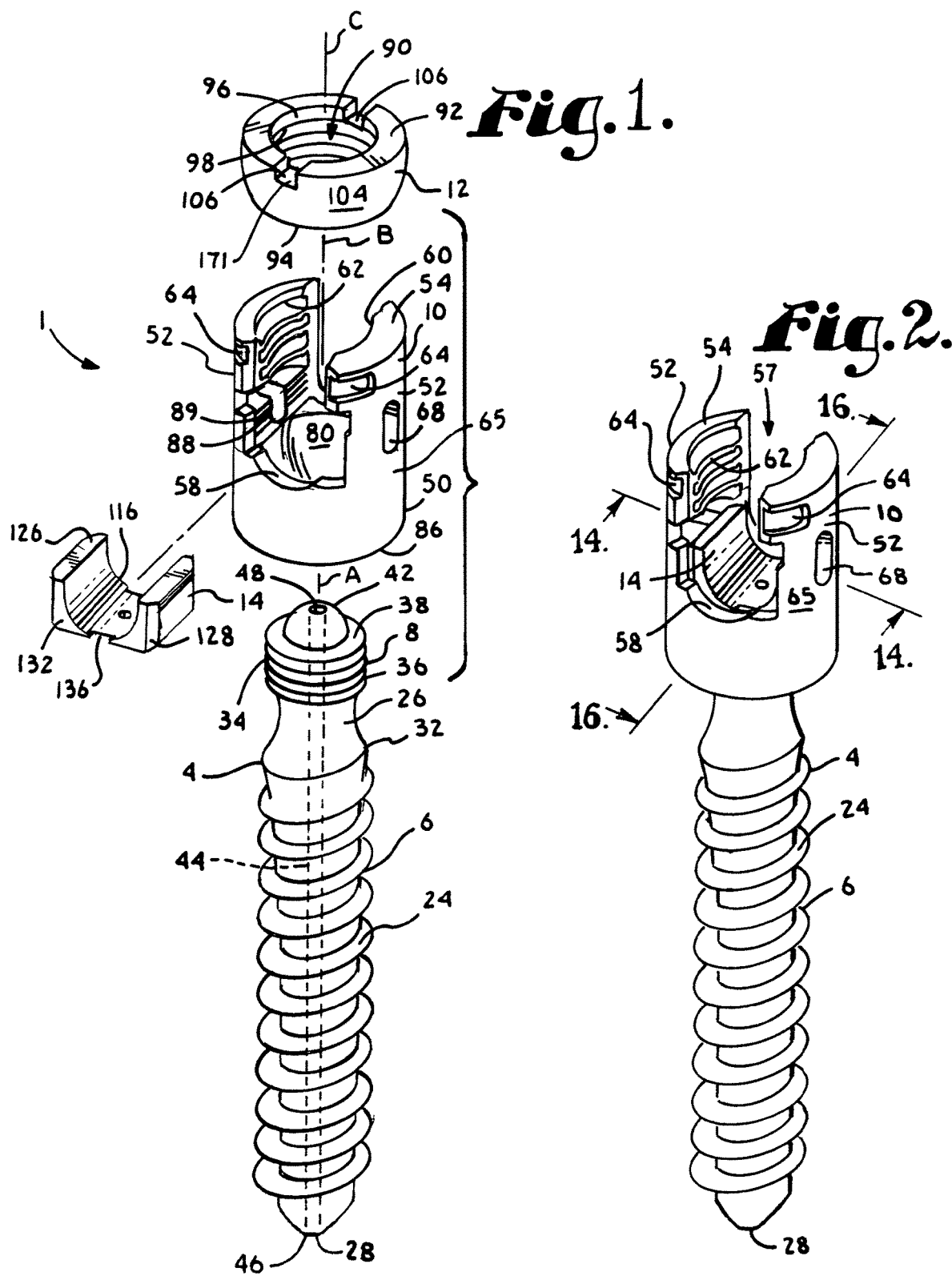

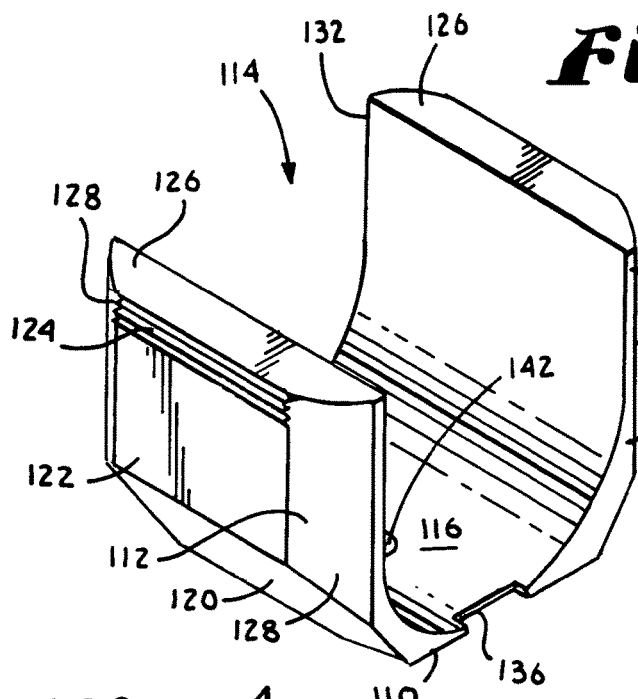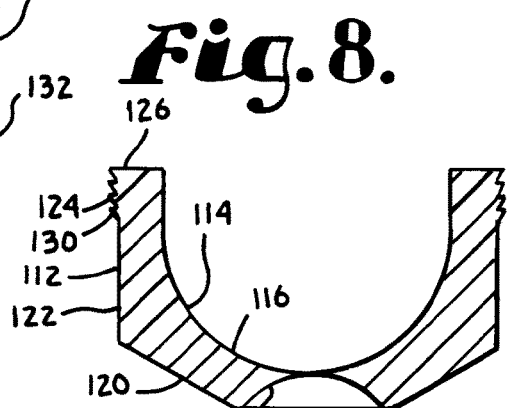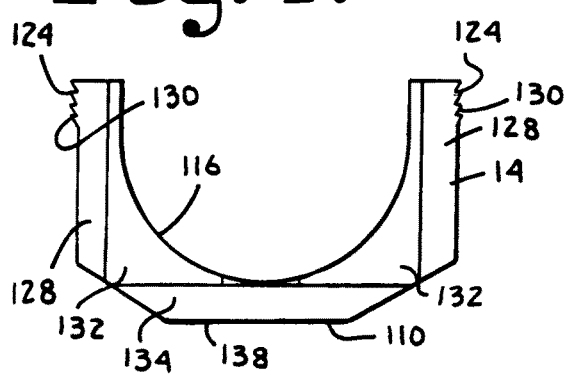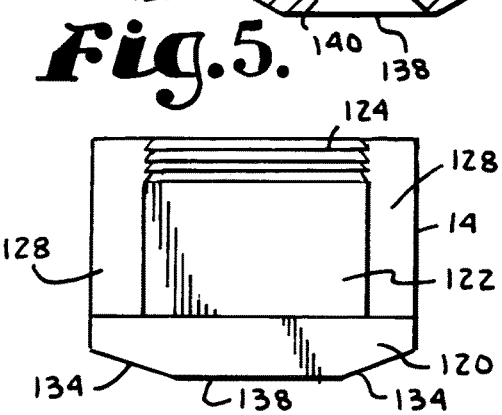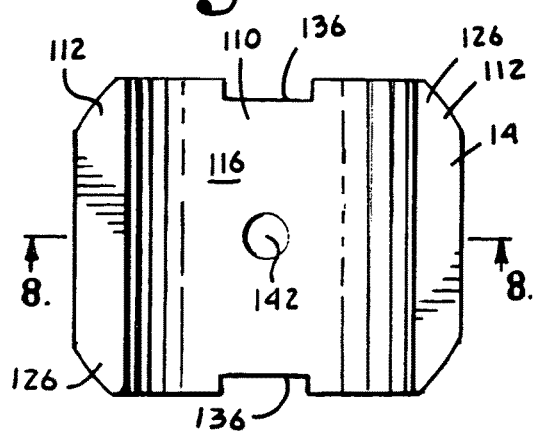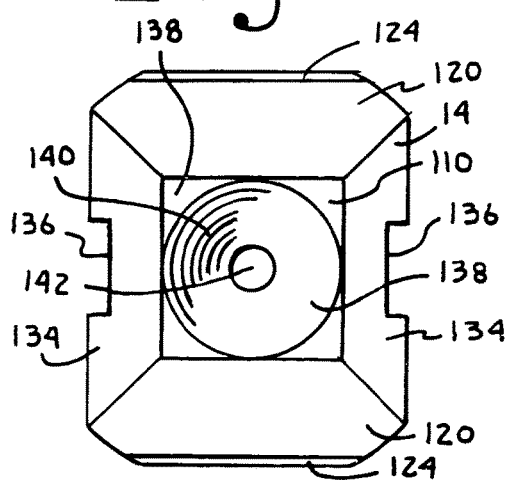

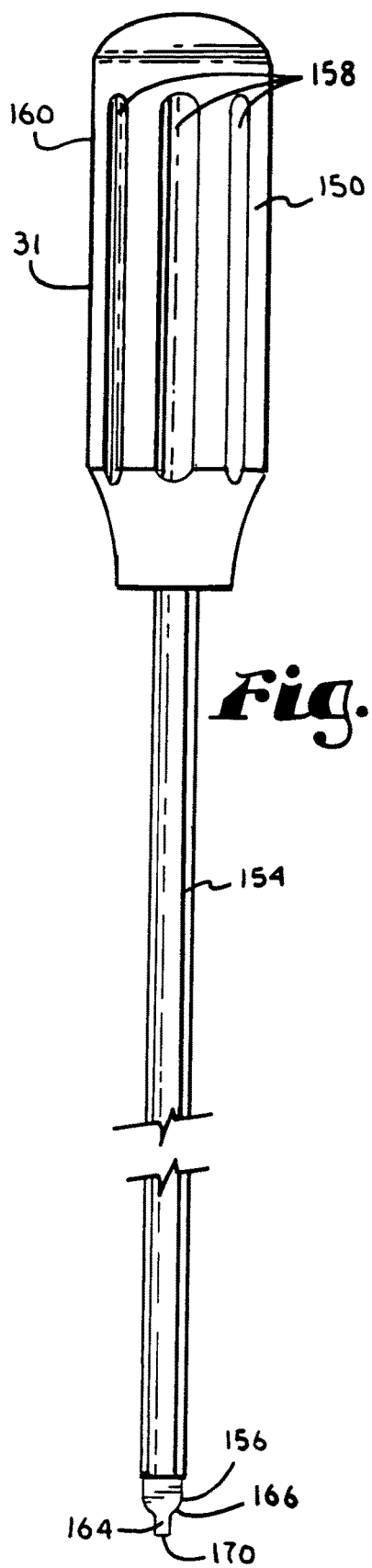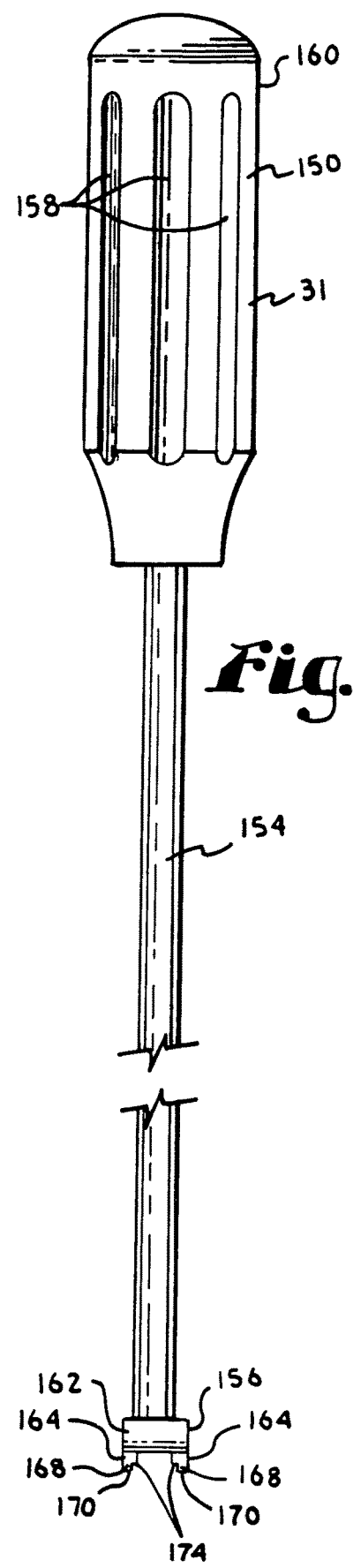

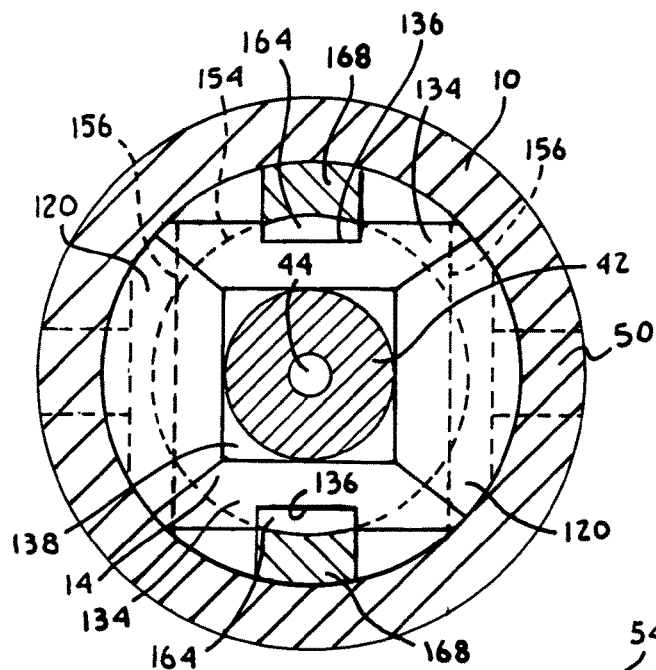
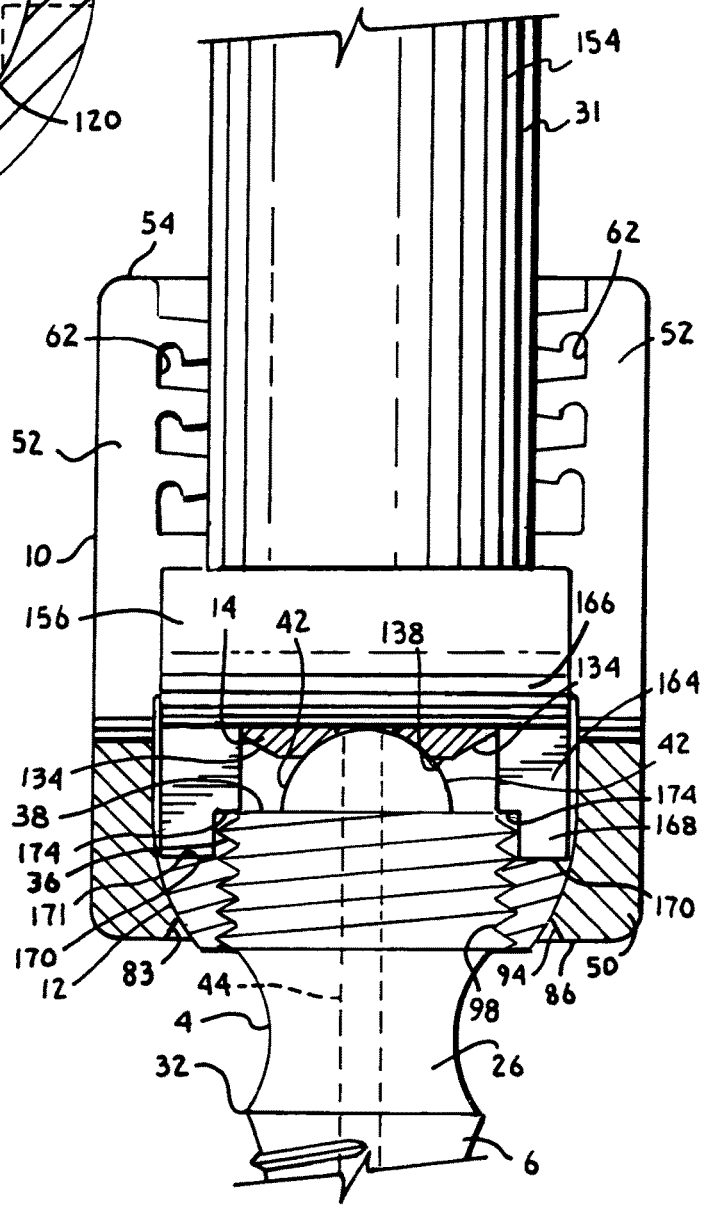

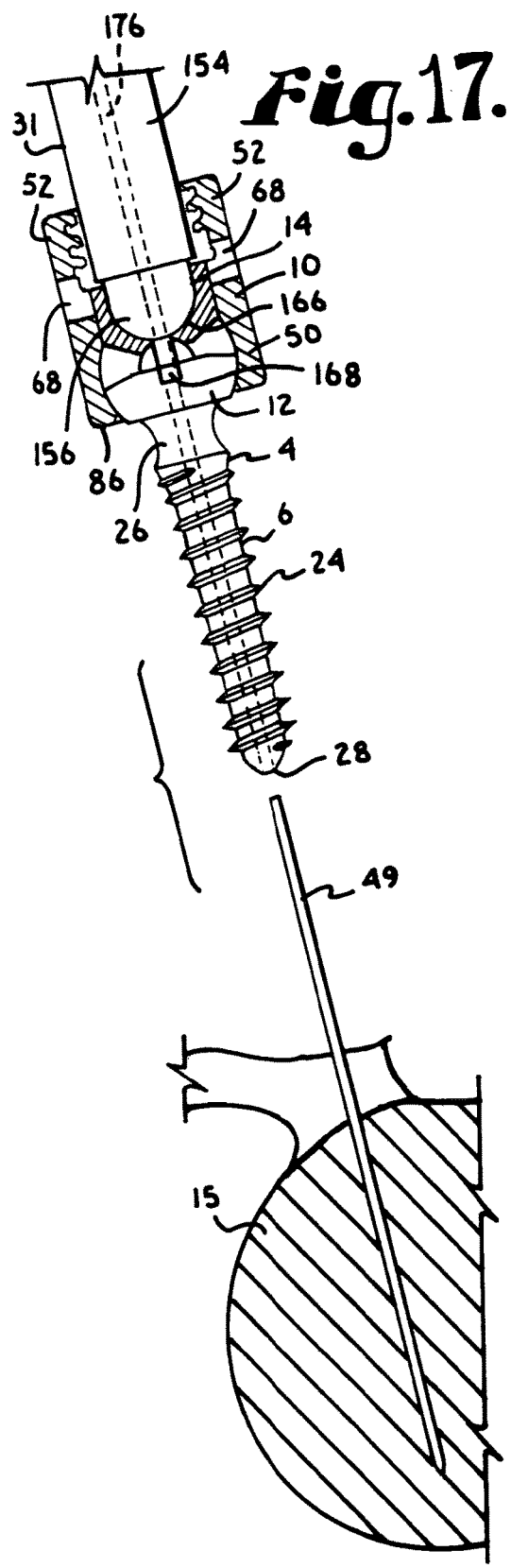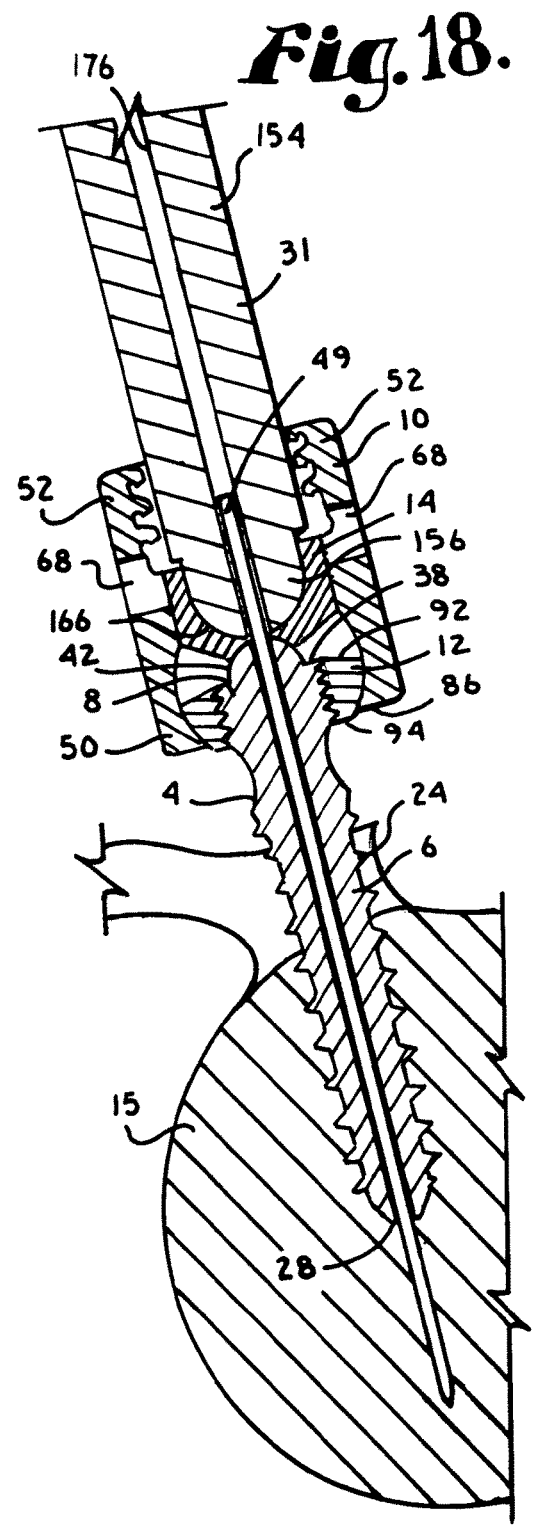

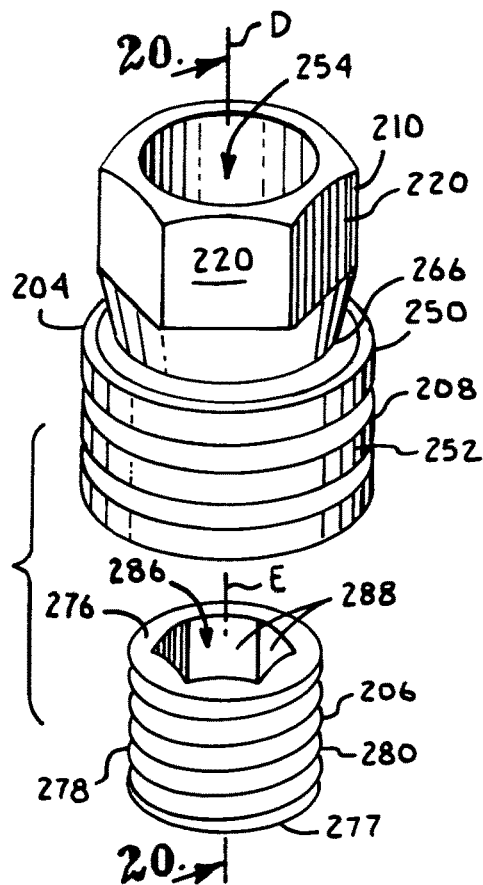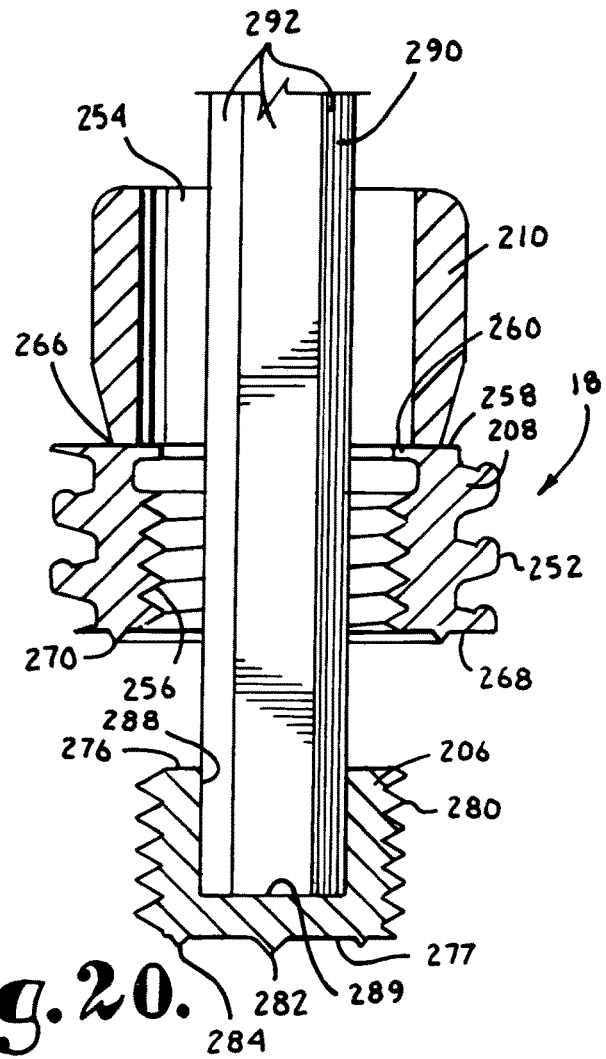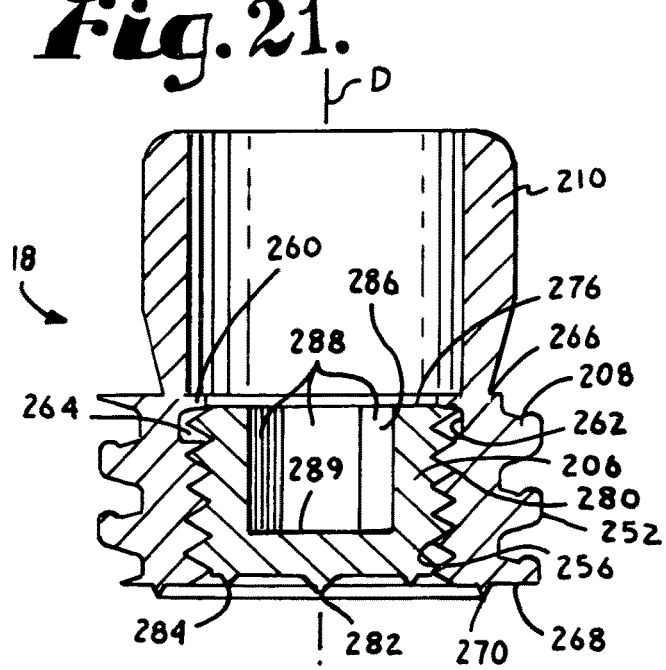

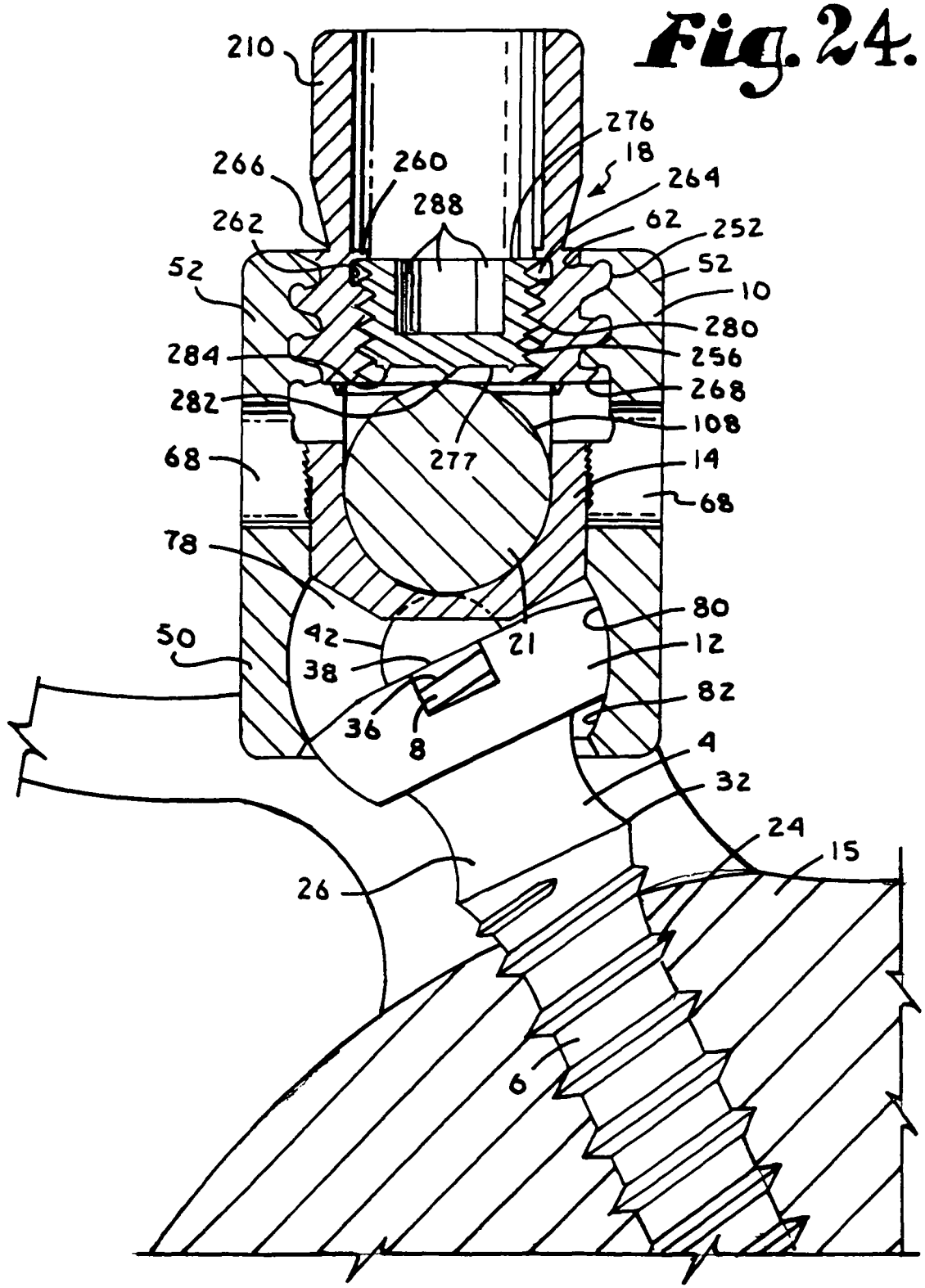

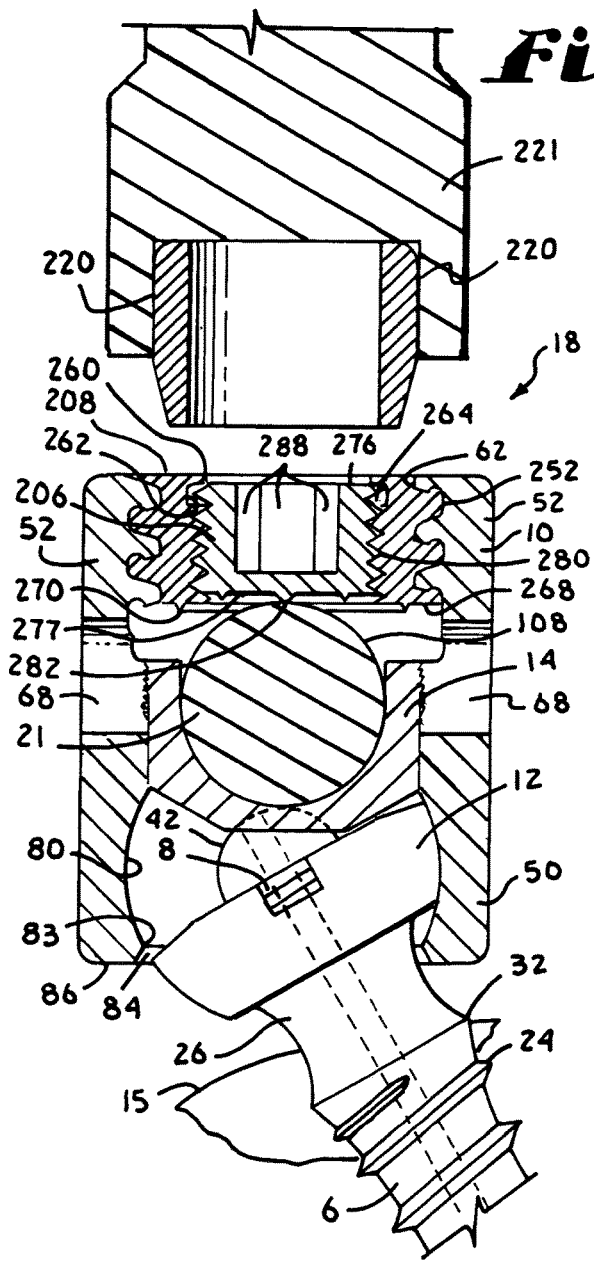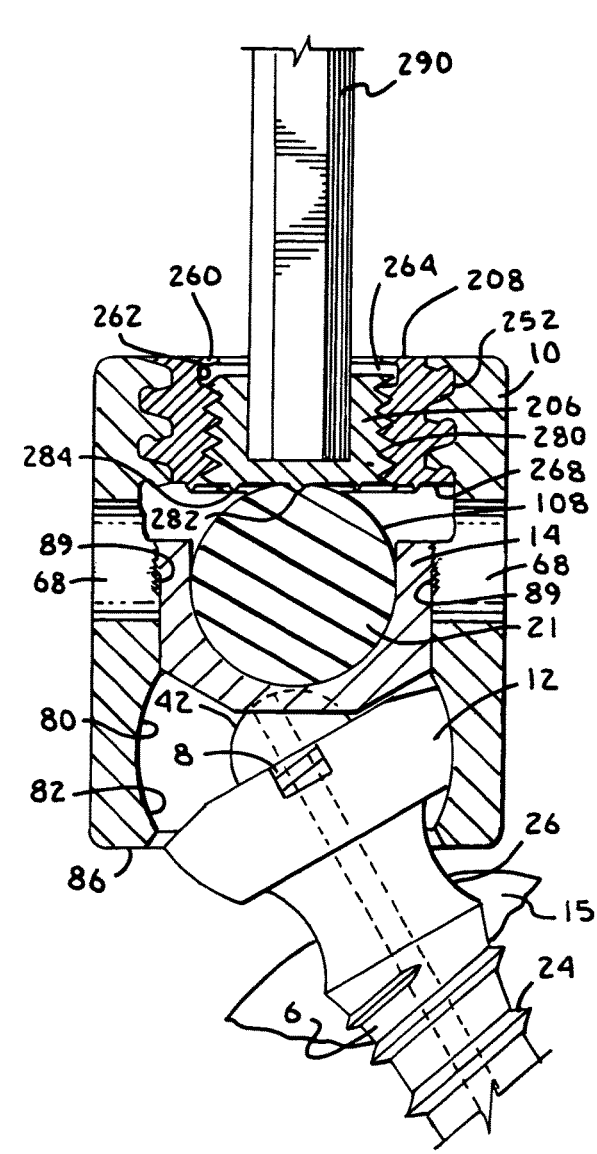

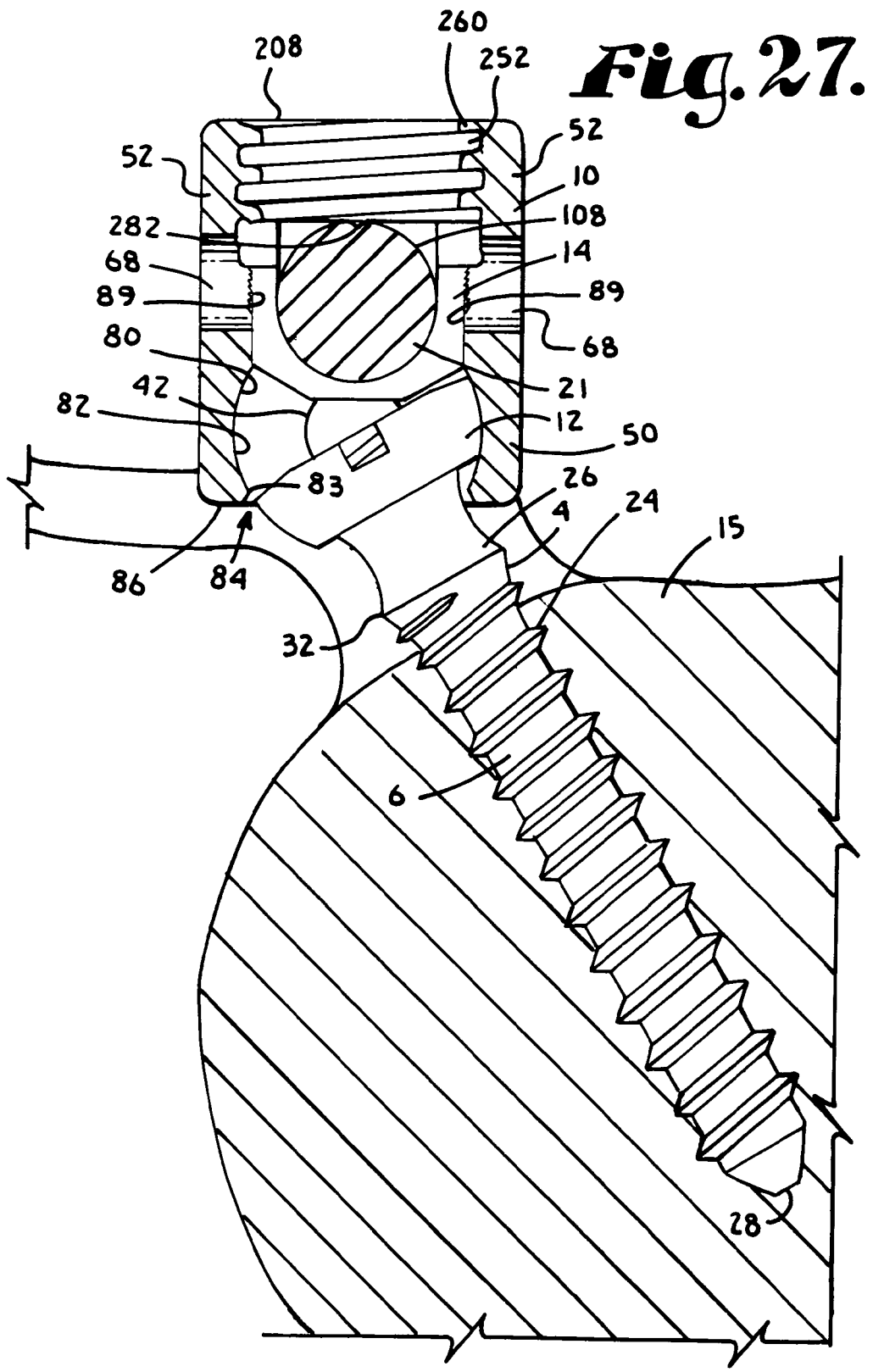

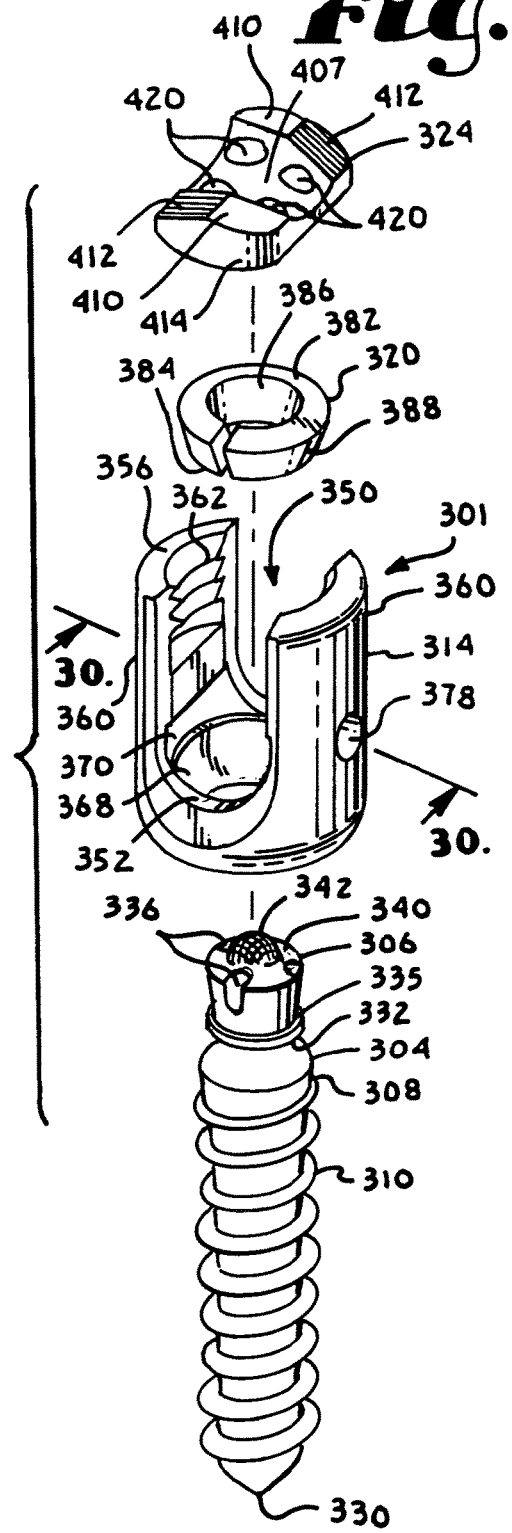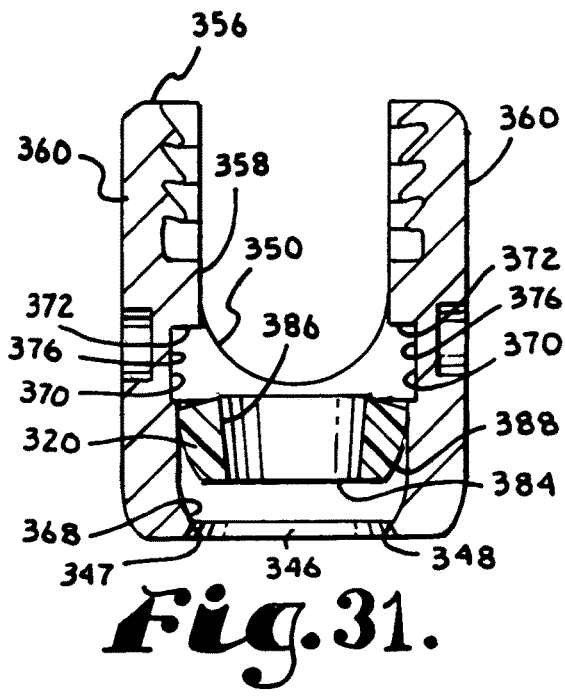
Fig. 29.
Fig. 30.
Fig. 31.

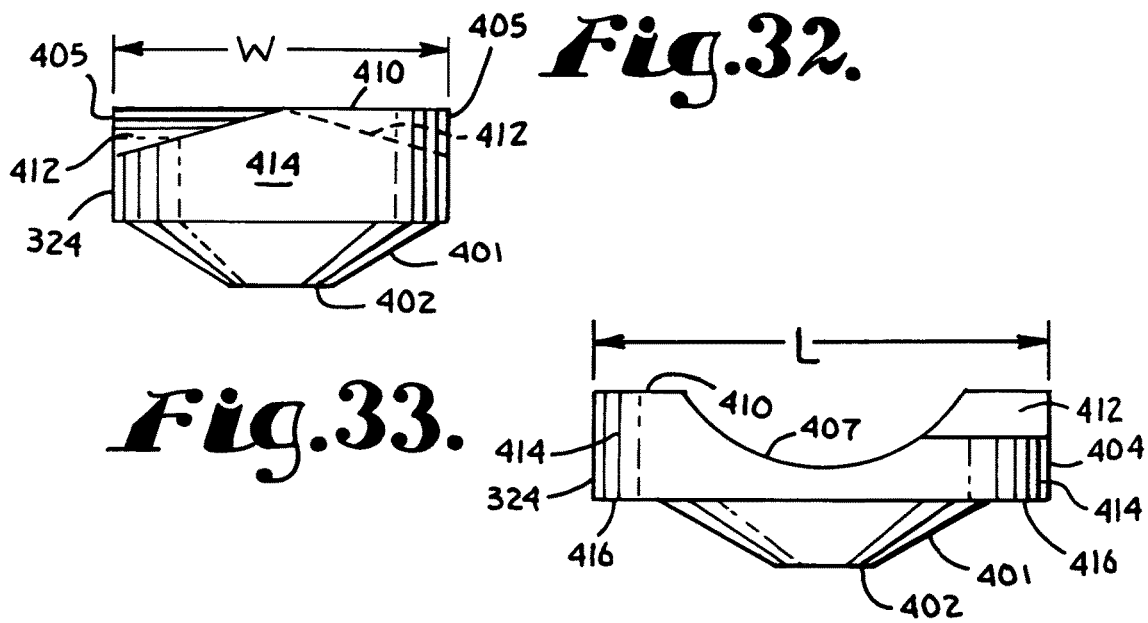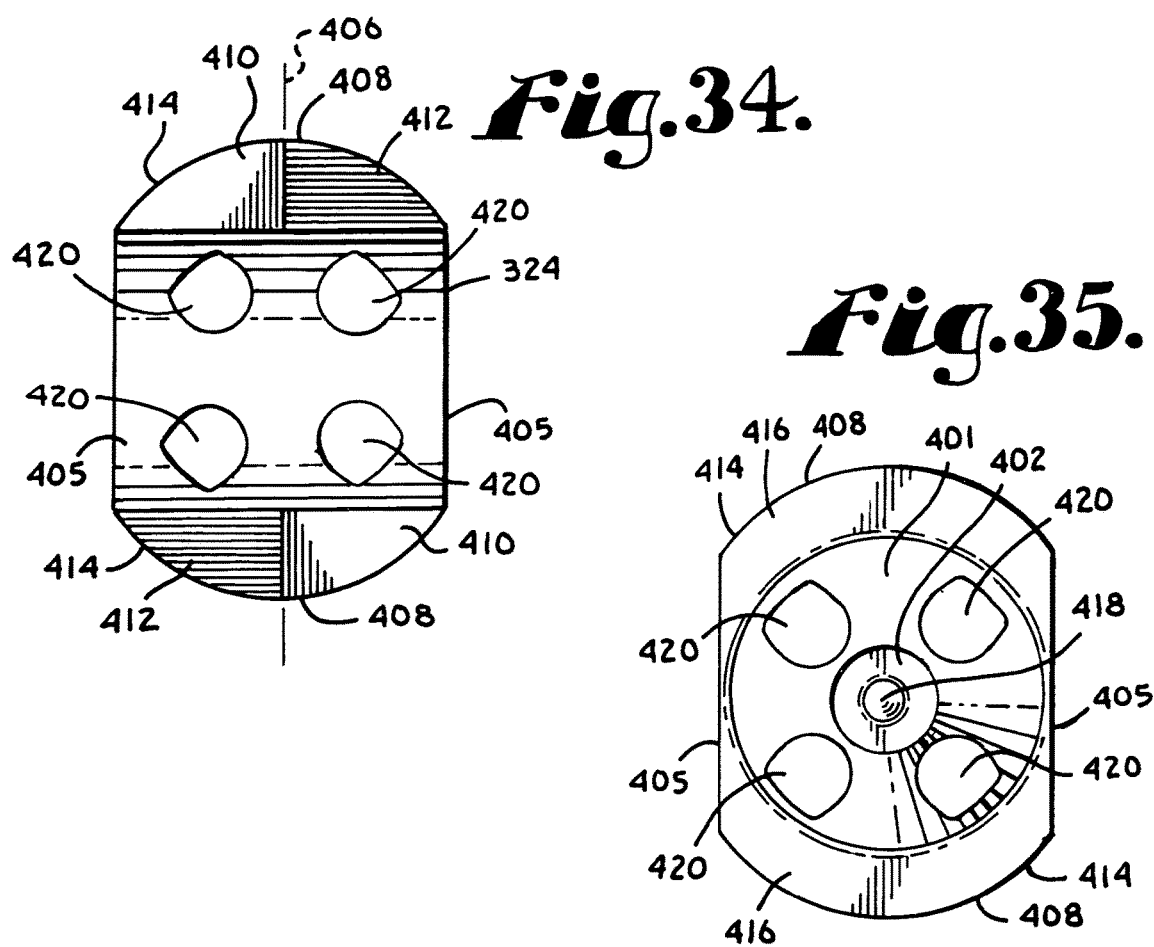

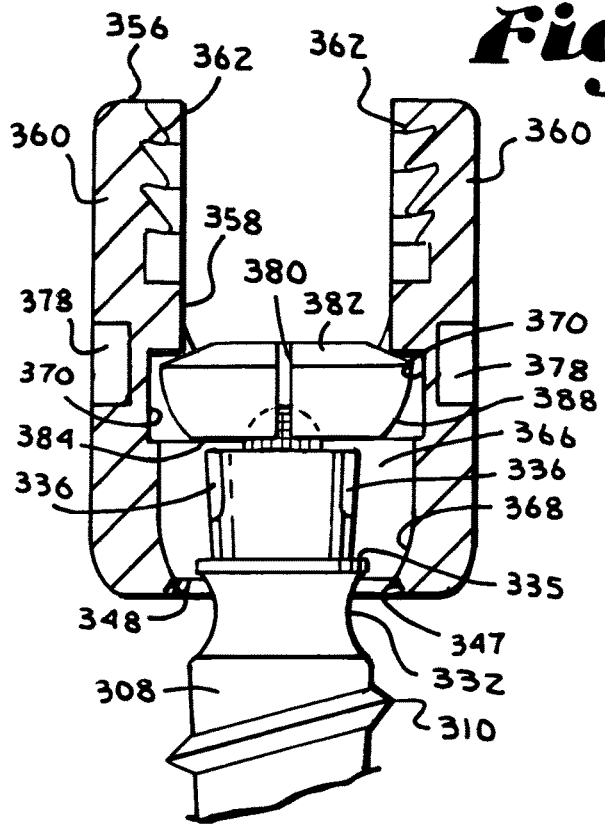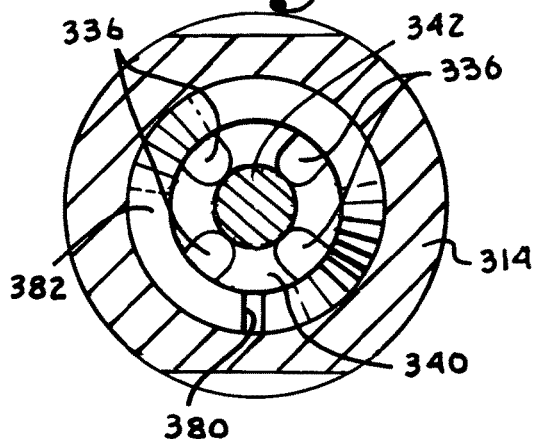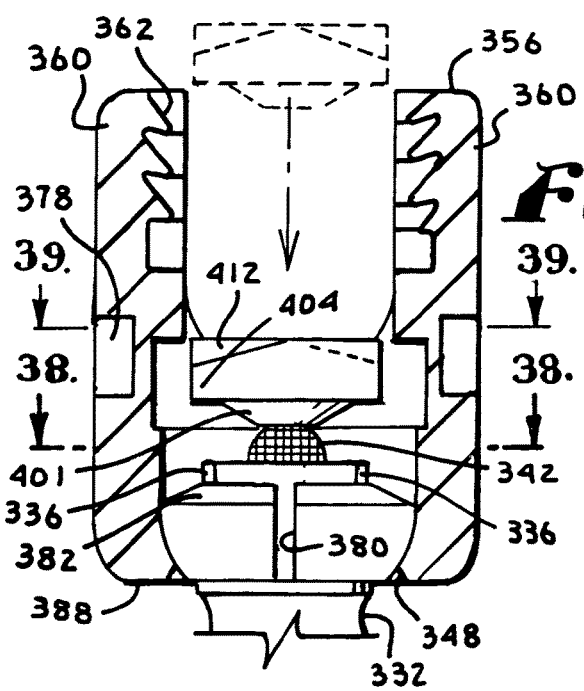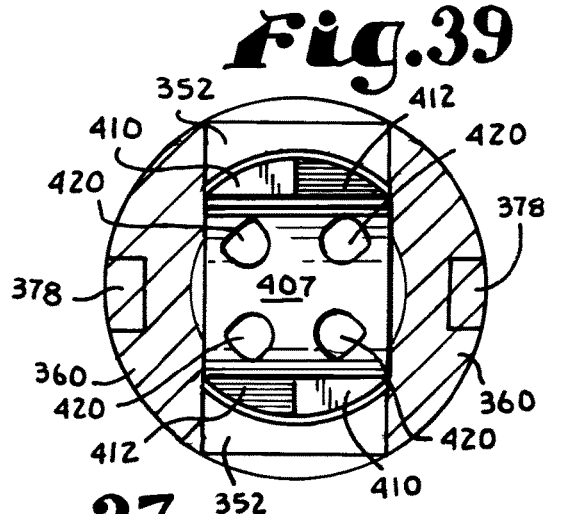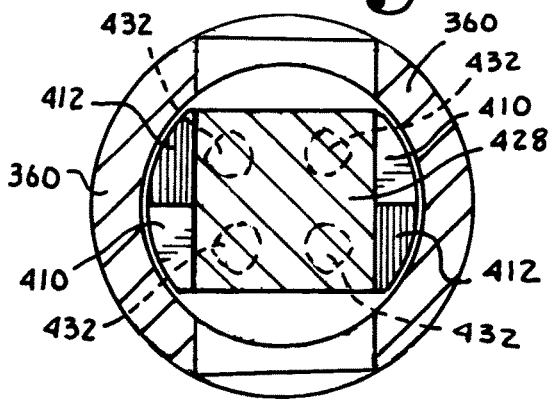

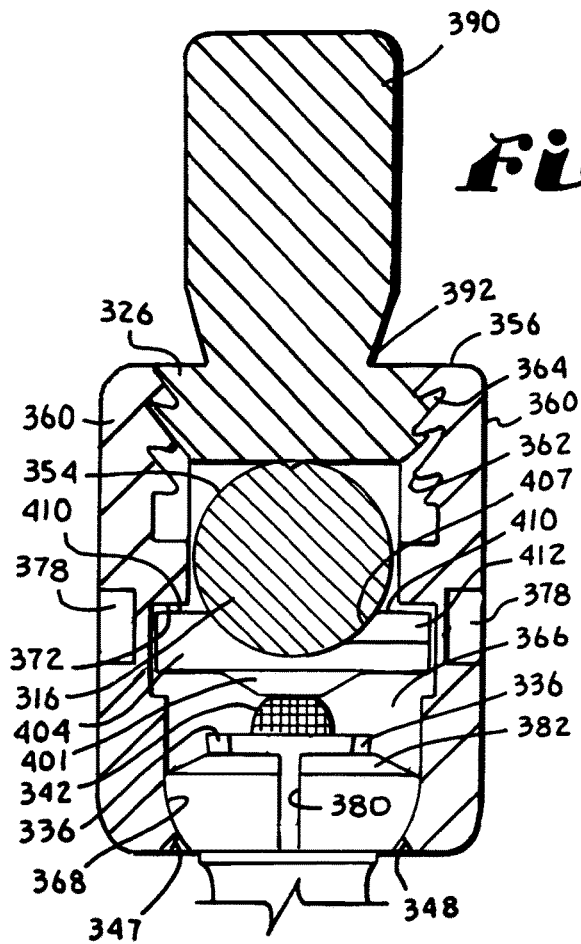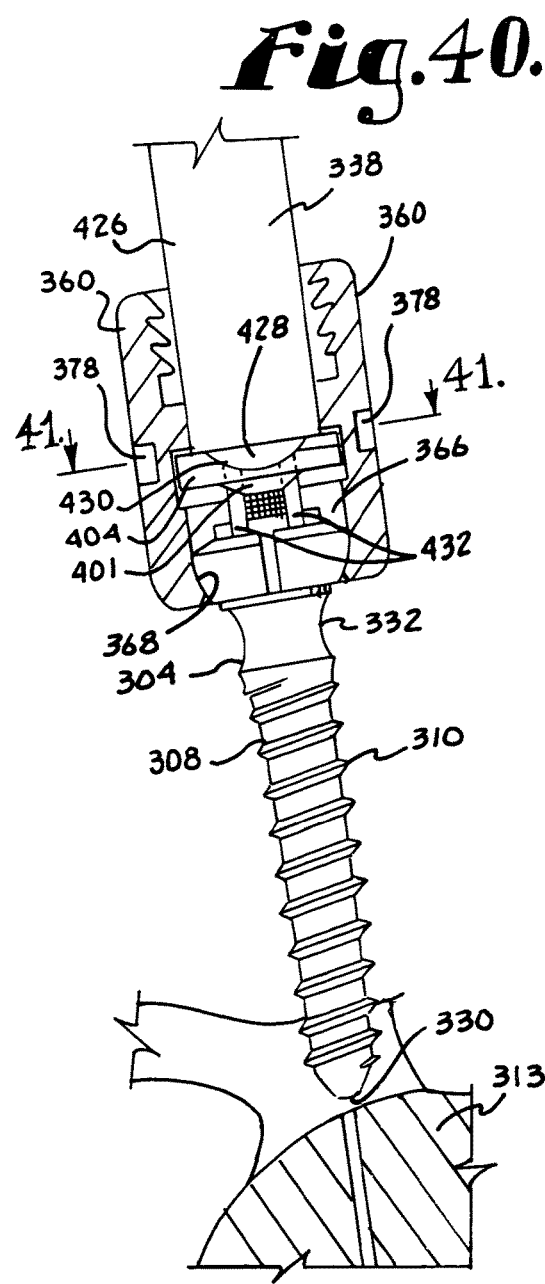

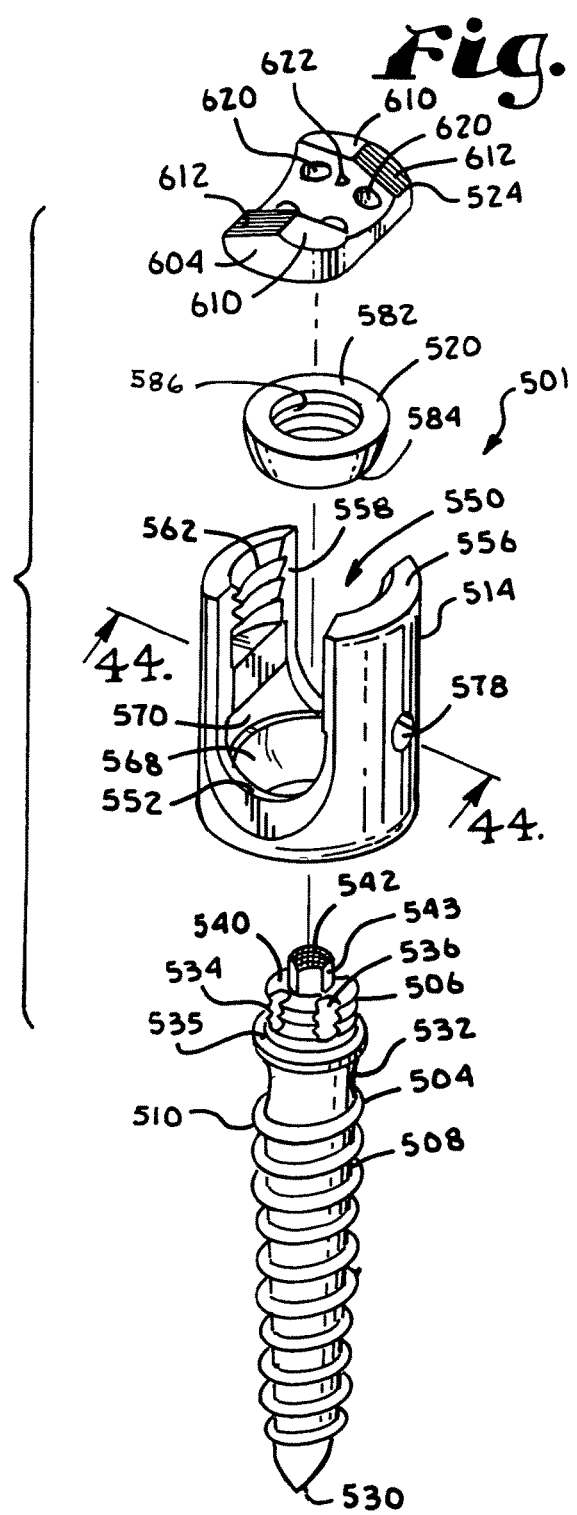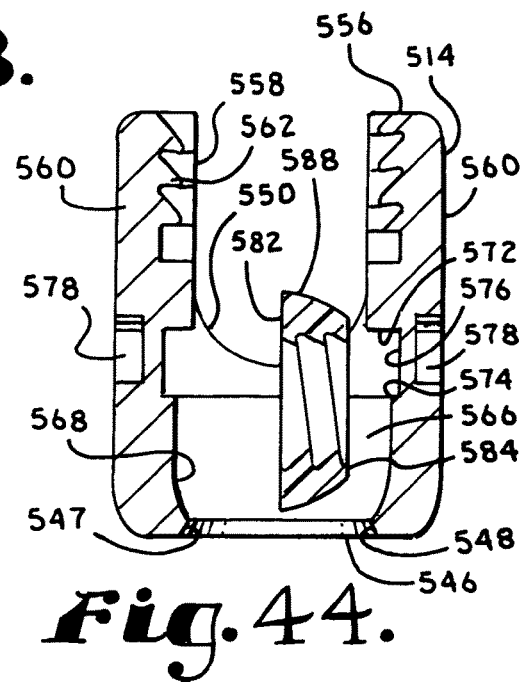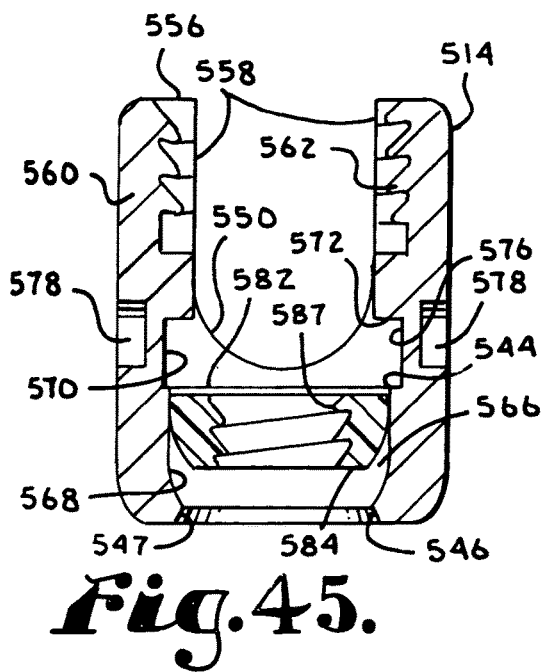

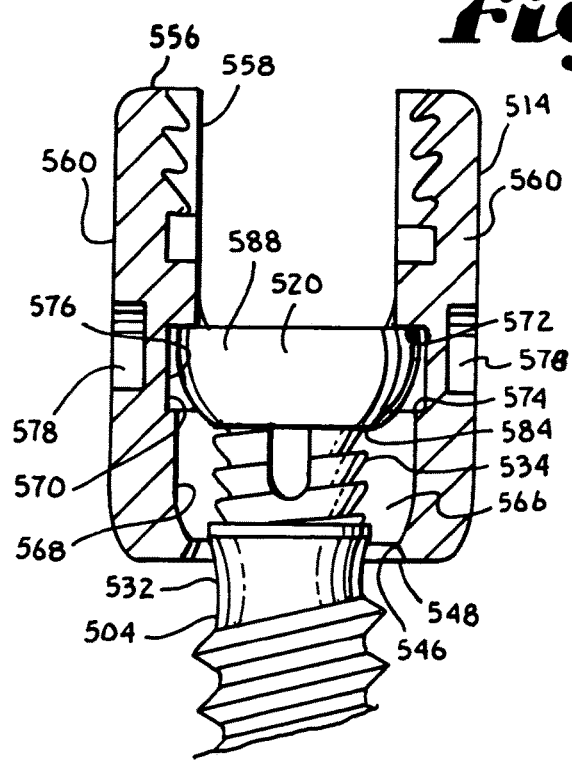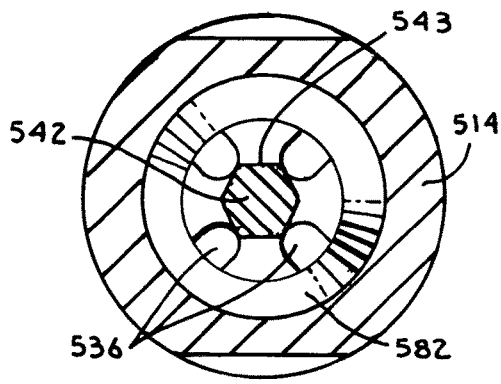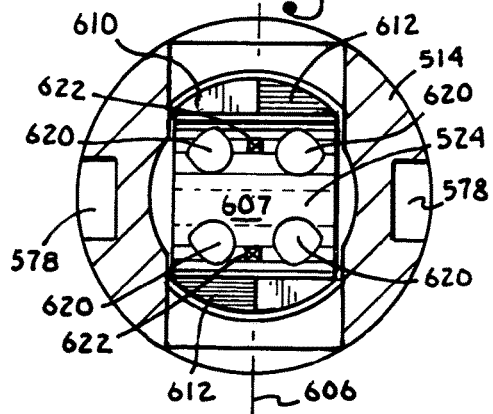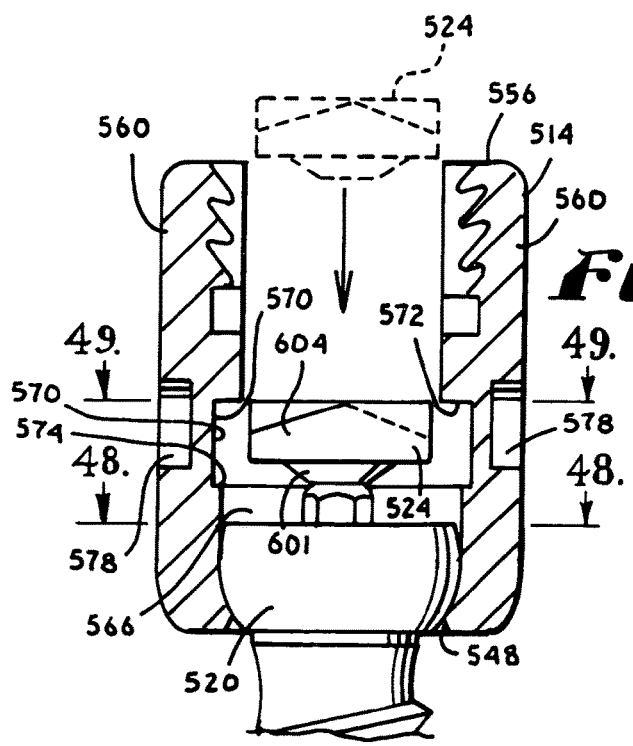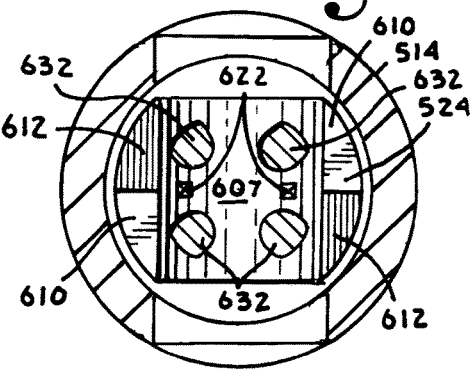

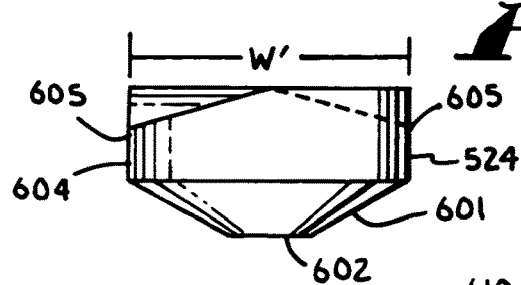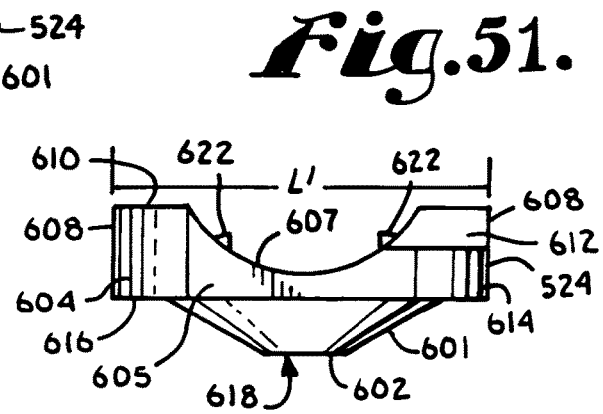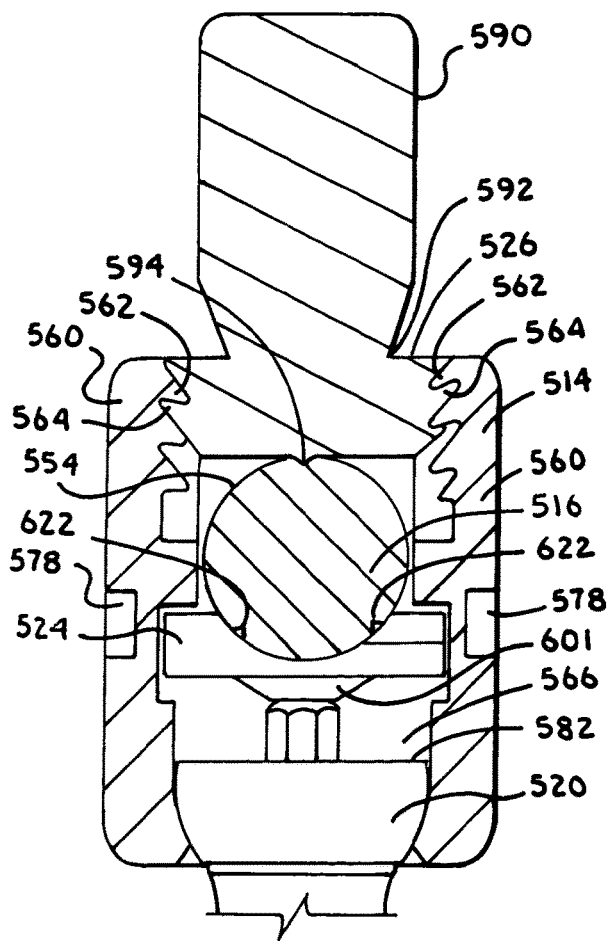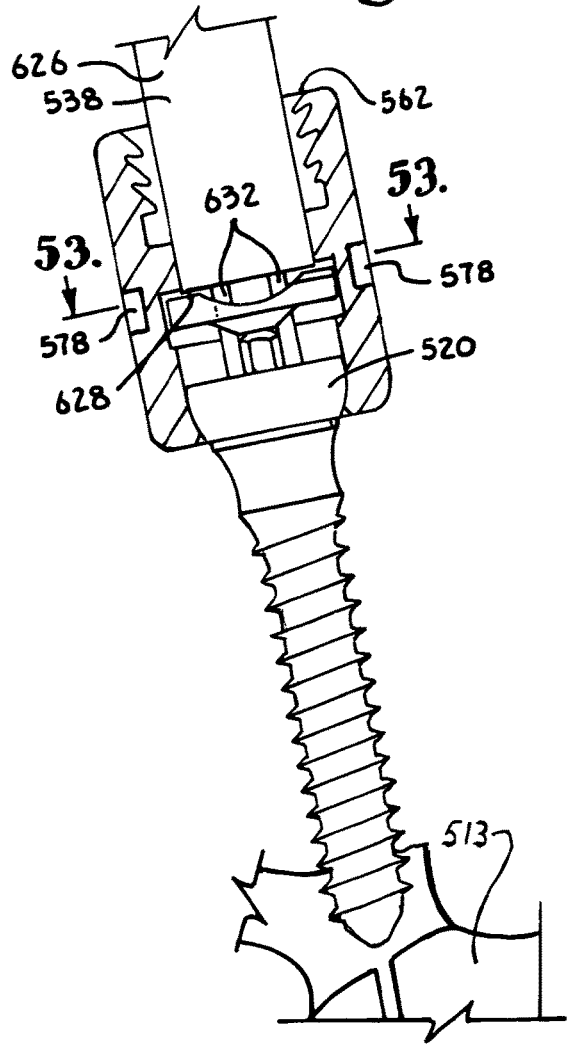

PIVOTAL BONE ANCHOR ASSEMBLY WITH RECEIVING AND LOCKING MEMBERS ENGAGEABLE BY INDEPENDENT LOCK AND RELEASE TOOLING

CROSS-REFERENCE TO RELATED APPLICATIONS

This application is a continuation of U.S. patent application Ser. No. 16/518,047 filed Jul. 22, 2019, which is a continuation of U.S. patent application Ser. No. 16/418,778, filed May 21, 2019, which is a continuation of U.S. patent application Ser. No. 16/371,423, filed Apr. 1, 2019, which is a continuation of U.S. patent application Ser. No. 15/885,443, filed Jan. 31, 2018, now U.S. Pat. No. 10,245,078, which is a continuation of U.S. patent application Ser. No. 15/703,567, filed Sep. 13, 2017, now U.S. Pat. No. 10,278,739, which is a continuation of U.S. patent application Ser. No. 15/702,442, filed Sep. 12, 2017, now U.S. Pat. No. 10,064,660, which is a continuation of U.S. patent application Ser. No. 15/401,618, filed Jan. 9, 2017, now U.S. Pat. No. 9,788,866, which is a continuation of U.S. patent application Ser. No. 15/094,870, filed Apr. 8, 2016, now U.S. Pat. No. 9,801,665, which is a continuation of U.S. patent application Ser. No. 14/026,150, filed Sep. 13, 2013, now U.S. Pat. No. 9,308,027, which is a continuation of U.S. patent application Ser. No. 12/802,668, filed Jun. 11, 2010, now U.S. Pat. No. 9,456,853, which is a continuation of U.S. patent application Ser. No. 11/140,343, filed May 27, 2005, now U.S. Pat. No. 7,776,067, each of which is incorporated by reference in its entirety herein, and for all purposes.

BACKGROUND OF THE INVENTION

The present invention is directed to polyaxial bone screws for use in bone surgery, particularly spinal surgery, and particularly to inserts for such screws.

Bone screws are utilized in many types of spinal surgery, such as for osteosynthesis, in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred.

Open-ended polyaxial bone screws allow rotation of the head or receiver about the shank until a desired rotational position of the head is achieved relative to the shank. Thereafter, a rod can be inserted into the head or receiver and eventually the head is locked or fixed in a particular position relative to the shank. However, in certain instances, a surgeon may desire to set and fix the angular position of the head or receiver relative to the shank independently of rod insertion or rod locking. Additionally, it may be desirable to reset and fix the angle of orientation of the head or receiver during the surgical procedure.

SUMMARY OF THE INVENTION

A polyaxial bone screw assembly according to the invention includes a shank having an upper portion and a body for fixation to a bone; a head or receiver defining an open channel; and at least one compression or pressure insert. The shank is connected to the head or receiver at the upper portion and the shank body is swivelable with respect to the head or receiver. The pressure insert is receivable in the head open channel. The pressure insert includes a base and a head engagement structure. The pressure insert base is frictionally engageable with the shank upper portion and the head engagement structure is engageable with the receiver head engagement structure. The pressure insert has an articulation position wherein the insert head engagement structure is engaged with the head and the base frictionally engages a projecting end of the shank upper portion with the pressure insert exerting an independent force or pressure on the shank upper portion sufficient to retain the shank body in a selected angle with respect to the head without continuously applied compression by a closure top through the rod.

Pressure inserts according to the invention include a side loading insert having a ratcheted outer surface for engagement with a ratcheted inner surface on the bone screw receiver head. Another embodiment includes a cam insert, side loaded or down loaded into the bone screw receiver head, having sloped upper surfaces for engagement with an upper shoulder of a recess formed in the bone screw receiver head.

OBJECTS AND ADVANTAGES OF THE INVENTION

Therefore, objects of the present invention include: providing an improved spinal implant assembly for implantation into vertebrae of a patient; providing such an assembly that includes an open-headed implant, a shank pivotally connected to the implant head, a rod or other structural element, and a pressure insert disposed between the shank and the rod; providing a pressure insert that may be utilized independently to set an angle of articulation of the shank with respect to the head prior to or after insertion of the rod; providing such an assembly that has a low profile after final installation; providing such an assembly in which the pressure insert may be assembled into a bone screw head prior or subsequent to installing the bone screw into bone; providing such an assembly in which the bone screw includes a retaining structure that includes a non-slip feature for driving the shank into bone; and providing such an assembly that is easy to use, especially adapted for the intended use thereof and wherein the implant assembly components are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of an assembly according to the invention including a shank with a capture structure at one end thereof, a head or receiver, a retaining and articulating structure and a side-loading pressure insert.

FIG. 2 is a perspective view of the assembly of FIG. 1 shown assembled.

FIG. 3 is an enlarged, perspective view of the insert of FIG. 1.

FIG. 4 is a front elevational view of the insert of FIG. 3.

FIG. 5 is a side elevational view of the insert of FIG. 3.

FIG. 6 is a top plan view of the insert of FIG. 3.

FIG. 7 is a bottom plan view of the insert of FIG. 3.

FIG. 8 is a cross-sectional view of the insert taken along the line 8-8 of FIG. 6.

FIG. 12 is a partial front elevational view of a bone screw driving tool according to the invention.

FIG. 13 is a partial side elevational view of the bone screw driving tool of FIG. 12.

FIG. 15 is a cross-sectional view taken along the line 15-15 of FIG. 14.

FIG. 16 is an enlarged and partial cross-sectional view of the head, retaining and articulating structure and insert taken along the line 16-16 of FIG. 2, shown with the shank in front elevation and further shown with the driving tool of FIG. 12 shown in the side elevational view of FIG. 13.

FIG. 17 is a reduced view of the bone screw and driving tool of FIG. 14 further shown in exploded view with a guide wire and vertebra.

FIG. 18 is an enlarged view of the bone screw, driving tool, guide wire and vertebra of FIG. 17 shown in cooperation during a process of bone screw installation.

FIG. 19 is an exploded perspective view of a nested bone screw fastener assembly including a fastener base integral with a break-off head and an inner set screw.

FIG. 20 is an enlarged cross-sectional view taken along the line 20-20 of FIG. 19 and shown with a set screw tool.

FIG. 21 is a cross-sectional view similar to FIG. 20, showing the set screw inserted in the fastener base.

FIG. 24 is a partial cross-sectional view, similar to FIGS. 22 and 23, shown with the shank fixed at a selected angle with respect to the head by frictional contact with the insert prior to frictional contact between the rod and the nested fastener assembly.

FIG. 25 is a reduced partial and cross-sectional view similar to FIG. 24, showing the break-off head of the nested closure assembly being removed with a torquing tool.

FIG. 26 is a partial cross-sectional view similar to FIG. 25 shown with a set screw tool engaged with the inner set screw in a process of tightening the set screw against the rod.

FIG. 27 is a cross-sectional view similar to FIG. 26 showing a fully installed nested fastener in front elevation.

FIG. 29 is an exploded perspective view of a second embodiment of an assembly according to the invention including a shank with a capture structure at one end thereof, a head, a retaining and articulating structure and an insert.

FIG. 30 is an enlarged cross-sectional view of the bone screw head and retaining and articulating structure taken along the line 30-30 of FIG. 29, shown with the retaining and articulating structure turned on a side thereof for insertion into the head.

FIG. 31 is a cross-sectional view similar to FIG. 30 showing the retaining and articulating structure turned back into the orientation shown in FIG. 29 but within the head in preparation for engagement with the capture structure of the shank.

FIG. 32 is an enlarged front elevational view of the insert of FIG. 29.

FIG. 33 is an enlarged side elevational view of the insert of FIG. 29.

FIG. 34 is an enlarged top plan view of the insert of FIG. 29.

FIG. 35 is an enlarged bottom plan view of the insert of FIG. 29.

FIG. 36 is an enlarged partial cross-sectional view of the head similar to FIG. 31 showing the shank and capture structure in front elevation in a process of engagement with the retaining and articulating structure, also shown in front elevation.

FIG. 37 is a partial cross-sectional view of the head similar to FIG. 36 showing the shank capture structure engaged with the retaining and articulating structure and showing a process of insertion of the insert into the head.

FIG. 38 is a cross-sectional view taken along the line 38-38 of FIG. 37.

FIG. 39 is a cross-sectional view taken along the line 39-39 of FIG. 37.

FIG. 40 is a reduced partial cross-sectional view of the head and front elevational view of the shank, retaining and articulating structure and insert similar to FIG. 37, showing the insert rotated to a shank setting position and the assembly in a process of being driven into bone with a driving tool.

FIG. 41 is an enlarged cross-sectional view taken along the line 41-41 of FIG. 40.

FIG. 42 is an enlarged and partial cross-sectional view of the head similar to FIG. 40, shown with the shank, retaining and articulating structure and insert in front elevation and further showing a rod in cross-section and an engaged closure top in front elevation.

FIG. 43 is an exploded perspective view of a third embodiment of an assembly according to the invention including a shank with a capture structure at one end thereof, a head, a retaining and articulating structure and an insert.

FIG. 44 is an enlarged cross-sectional view of the bone screw head and retaining and articulating structure taken along the line 44-44 of FIG. 43, shown with the retaining and articulating structure turned on a side thereof for insertion into the head.

FIG. 45 is a cross-sectional view similar to FIG. 44 showing the retaining and articulating structure turned back into the orientation shown in FIG. 43 but within the head in preparation for engagement with the capture structure of the shank.

FIG. 46 is a partial cross-sectional view of the head similar to FIG. 45 showing the shank and capture structure in front elevation in a process of engagement with the retaining and articulating structure, also shown in front elevation.

FIG. 47 is a partial cross-sectional view of the head similar to FIG. 46 showing the shank capture structure engaged with the retaining and articulating structure and showing a process of insertion of the insert into the head.

FIG. 48 is a cross-sectional view taken along the line 48-48 of FIG. 47.

FIG. 49 is a cross-sectional view taken along the line 49-49 of FIG. 47.

FIG. 50 is an enlarged front elevational view of the insert of FIG. 43.

FIG. 51 is an enlarged side elevational view of the insert of FIG. 43.

FIG. 52 is a reduced partial cross-sectional view of the head and front elevational view of the shank, retaining and articulating structure and insert similar to FIG. 47, showing the insert rotated to a shank setting position and the assembly in a process of being driven into bone with a driving tool.

FIG. 53 is an enlarged cross-sectional view taken along the line 53-53 of FIG. 52.

FIG. 54 an enlarged and partial cross-sectional view of the head similar to FIG. 52, shown with the shank, retaining and articulating structure and insert in front elevation and further showing a rod in cross-section and an engaged closure top in front elevation.

DETAILED DESCRIPTION OF THE INVENTION

Figure 9:
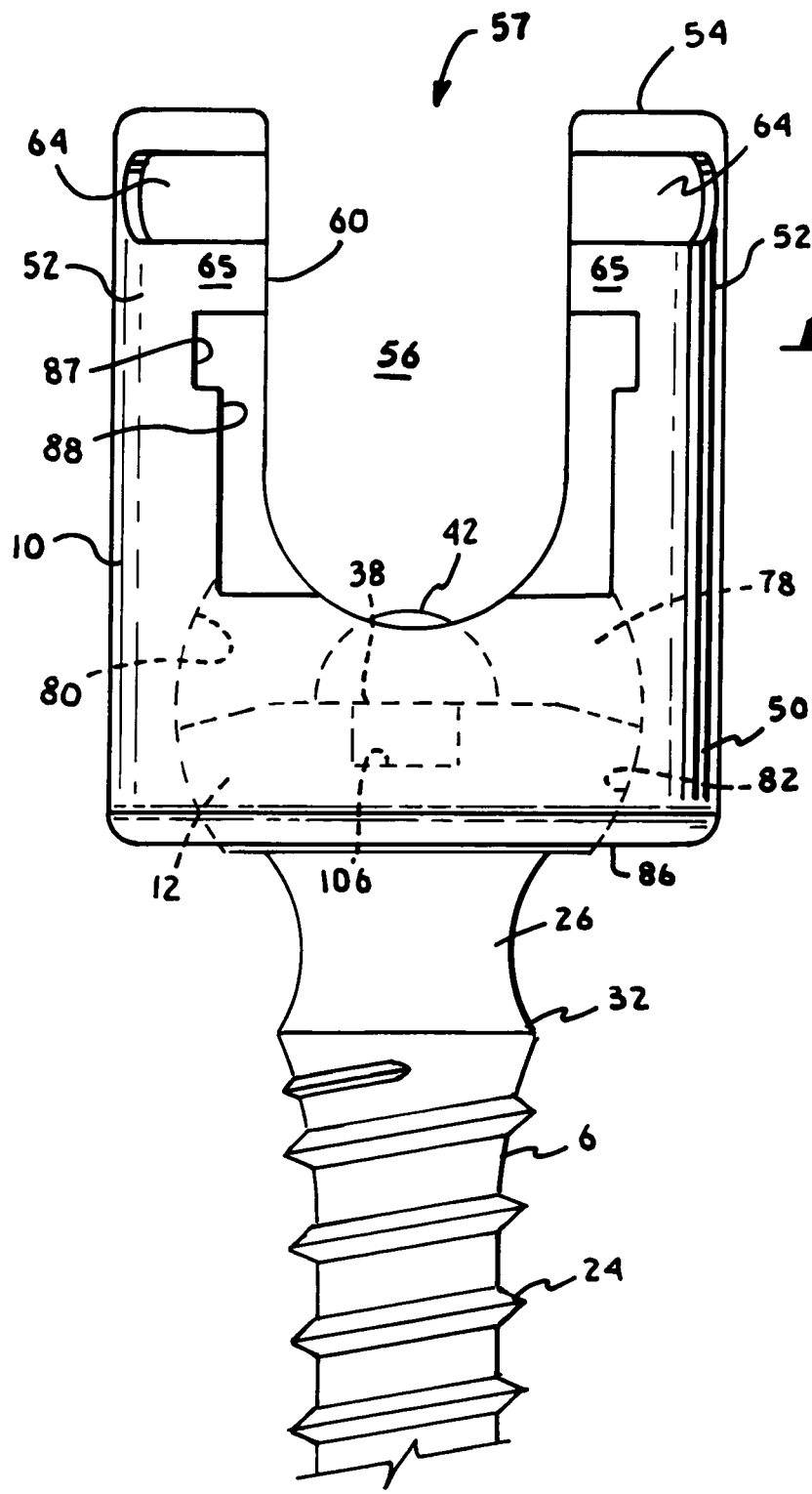
FIG. 9 is an enlarged and partial front elevational view of the assembled shank, bone screw head and retaining and articulating structure of FIG. 2 shown prior to insertion of the side-loading insert.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

With reference to FIGS. 1-28, the reference numeral 1 generally designates a polyaxial bone screw assembly according to the present invention. The assembly 1 includes a shank 4 that further includes a body 6 integral with an upwardly extending capture structure 8; a head or receiver 10; a retaining and articulating structure or ring 12; and a side-loading pressure insert 14. The shank 4, head or receiver 10, retaining and articulating structure 12 and insert 14 are preferably assembled prior to implantation of the shank body 6 into a vertebra 15, which procedure is shown in FIGS. 17 and 18.

FIGS. 19-28 further show a closure structure or nested fastener, generally 18, of the invention for capturing a longitudinal member such as a rod 21 within the head or receiver 10. The insert 14 allows for setting an angle of articulation between the shank body 6 and the head or receiver 10 prior to insertion of the rod 21, if desired. Upon installation, which will be described in detail below, the nested fastener 18 presses against the rod 21 that in turn presses against the insert 14 that presses against the capture structure 8 which biases the retaining and articulating structure 12 into fixed frictional contact with the head or receiver 10, so as to fix the rod 21 relative to the vertebra 15. The head or receiver 10 and shank 4 cooperate in such a manner that the head 10 and shank 4 can be secured at any of a plurality of angles, articulations or rotational alignments relative to one another and within a selected range of angles both from side to side and from front to rear, to enable flexible or articulated engagement of the head 10 with the shank 4 until both are locked or fixed relative to each other.

The shank 4, best illustrated in FIGS. 1 and 2, is elongate, with the shank body 6 having a helically wound bone implantable thread 24 extending from near a neck 26 located adjacent to the capture structure 8 to a tip 28 of the body 6 and extending radially outward therefrom. During use, the body 6 utilizing the thread 24 for gripping and advancement is implanted into the vertebra 15 leading with the tip 28 and driven down into the vertebra 15 with an installation or driving tool 31 so as to be implanted in the vertebra 15 to near the neck 26, as shown in FIG. 24, and as is described more fully in the paragraphs below. The shank 4 has an elongate axis of rotation generally identified by the reference letter A. It is noted that any reference to the words top, bottom, up and down, and the like, in this application refers to the alignment shown in the various drawings, as well as the normal connotations applied to such devices, and is not intended to restrict positioning of the assembly 1 in actual use.

The neck 26 extends axially outward and upward from the shank body 6. The neck 26 may be of reduced radius as compared to an adjacent top 32 of the body 6. Further extending axially and outwardly from the neck 26 is the capture structure 8 that provides a connective or capture structure disposed at a distance from the body top 32 and thus at a distance from the vertebra 15 when the body 6 is implanted in the vertebra 15.

The capture structure 8 is configured for connecting the shank 4 to the head or receiver 10 and capturing the shank 4 in the head 10. The capture structure 8 has an outer substantially cylindrical surface 34 having a helically wound guide and advancement structure thereon which in the illustrated embodiment is a V-shaped thread 36 extending from near the neck 26 to adjacent to an annular upper surface 38. Although a simple thread 36 is shown in the drawings, it is foreseen that other structures including other types of threads, such as buttress and reverse angle threads, and non threads, such as helically wound flanges with interlocking surfaces, may be alternatively used in alternative embodiments of the present invention.

Projecting along the axis A upwardly and outwardly from the annular surface 38 of the capture structure 8 is a curved or dome-shaped top 42. The illustrated top 42 is radially extending, convex, substantially hemispherical or dome-shaped, preferably having a substantially uniform radius of generation to provide for positive engagement with the insert 14 at almost any orientation of the shank 4, as will be described more fully below. It is foreseen that in certain embodiments the radius may vary depending upon the needs and desires of the particular structure and the domed top 42 may have a shape that is only partly spherical or some other shape. For example, the domed top could be radiused at the location of greatest projection along the axis A and otherwise feathered along a periphery thereof so as to not have a continuous uniform radius of generation throughout but rather a continually changing radius of generation along at least the length thereof.

The shank 4 shown in some of the drawings is cannulated, having a small central bore 44 extending an entire length of the shank 4 along the axis A. The bore 44 has a first circular opening 46 at the shank tip 28 and a second circular opening 48 at the top surface 42. The bore 44 is coaxial with the threaded body 6 and the capture structure outer surface 34. The bore 44 provides a passage through the shank 4 interior for a length of wire or pin 49 as shown in FIGS. 17 and 18, inserted into the vertebra 15 prior to the insertion of the shank body 6, the pin 49 providing a guide for insertion of the shank body 6 into the vertebra 15.

Referring to FIGS. 1, 2, 9-11 and 14, the head or receiver 10 has a generally cylindrical outer profile with a substantially cylindrical base 50 integral with a pair of opposed upstanding arms 52 that extend from the base 50 to a top surface 54. The arms 52 form a U-shaped cradle and define a U-shaped channel 56 between the arms 52 and include an upper opening 57 and a lower seat 58 having substantially the same radius as the rod 21 for operably snugly receiving the rod 21.

Each of the arms 52 has an interior surface 60 that defines the inner cylindrical profile and includes a partial helically wound guide and advancement structure 62. In the illustrated embodiment, the guide and advancement structure 62 is a partial helically wound flangeform configured to mate under rotation with a similar structure on the nested fastener 18, as described more fully below. However, it is foreseen that the guide and advancement structure 62 could alternatively be a V-shaped thread, a buttress thread, a square thread, a reverse angle thread or other thread like or non-thread like helically wound advancement structures for operably guiding under rotation and advancing the fastener 18 downward between the arms 52.

Tool engaging grooves 64 are formed on outer substantially cylindrical surfaces 65 of the arms 52 which may be used for holding the head 10 during assembly with the shank 4 and the retaining and articulating structure 12 and also during the implantation of the shank body 6 into vertebra 15. The illustrated grooves 64 are disposed near the top 54 of the head 10 and each extend partially circumferentially about a periphery of each arm 52 and may include an undercut or dovetail feature for engagement with a holding tool. A holding tool (not shown) is equipped with structure sized and shaped to be received in the grooves 64. The holding tool and respective grooves 64 may be configured for either a twist on/twist off engagement with the head, or a flexible snap on/snap off engagement wherein the holding tool has legs which splay outwardly to position the tool for engagement in the grooves 64 or a combination thereof. It is foreseen that the grooves 64 and the cooperating holding tool may be configured to be of a variety of sizes and locations along the cylindrical surfaces 65. Also disposed centrally on each arm 52 is an oval through-bore 68 that allows for manipulation of the insert 14 as will be described more fully below.

Communicating with the U-shaped channel 56 and located within the base 50 of the head or receiver 10 is a chamber or cavity 78 substantially defined by an inner surface 80 of the base 50, the cavity 78 opening upwardly into the U-shaped channel 56. The inner surface 80 is substantially spherical, with at least a portion thereof forming a partial internal spherical seating surface 82 having a first radius. The surface 82 is sized and shaped for mating with the retaining and articulating structure 12, as described more fully below.

The base 50 further includes a restrictive neck 83 defining a bore 84 communicating with the cavity 78 and a lower exterior 86 of the base 50. The bore 84 is coaxially aligned with respect to a rotational axis B of the head 10. The bore 84 may be conically counterbored or beveled in a region 85 to widen the angular range of the shank 4.

The neck 83 and associated bore 84 are sized and shaped to be smaller than a radial dimension of the retaining and articulating structure 12, as will be discussed further below, so as to form a restriction at the location of the neck 83 relative to the retaining and articulating structure 12, to prevent the retaining and articulating structure 12 from passing from the cavity 78 and out into the lower exterior 86 of the head 10 when the retaining and articulating structure 12 is seated. However, it is foreseen that the retaining and articulating structure could be compressible (such as where such structure has a missing section) and that the retaining structure could be loaded up through the neck 83 and then allowed to expand and fully seat in the spherical seating surface.

It is foreseen that the inner surface 80 may further include an elongate upper loading recess (not shown) for accommodating and loading the retaining and articulating structure 12 into the cavity 78. Such a loading recess would be generally vertically disposed in the head 10, extending between and communicating with both the channel 56 and the cavity 78, allowing for ease in top loading the retaining and articulating structure 12 into the cavity through the upper opening 57 and otherwise allowing for the spherical wall 80 of the head 10 to have a radius allowing for substantial thickness and strength of the head base 50.

Figure 10:
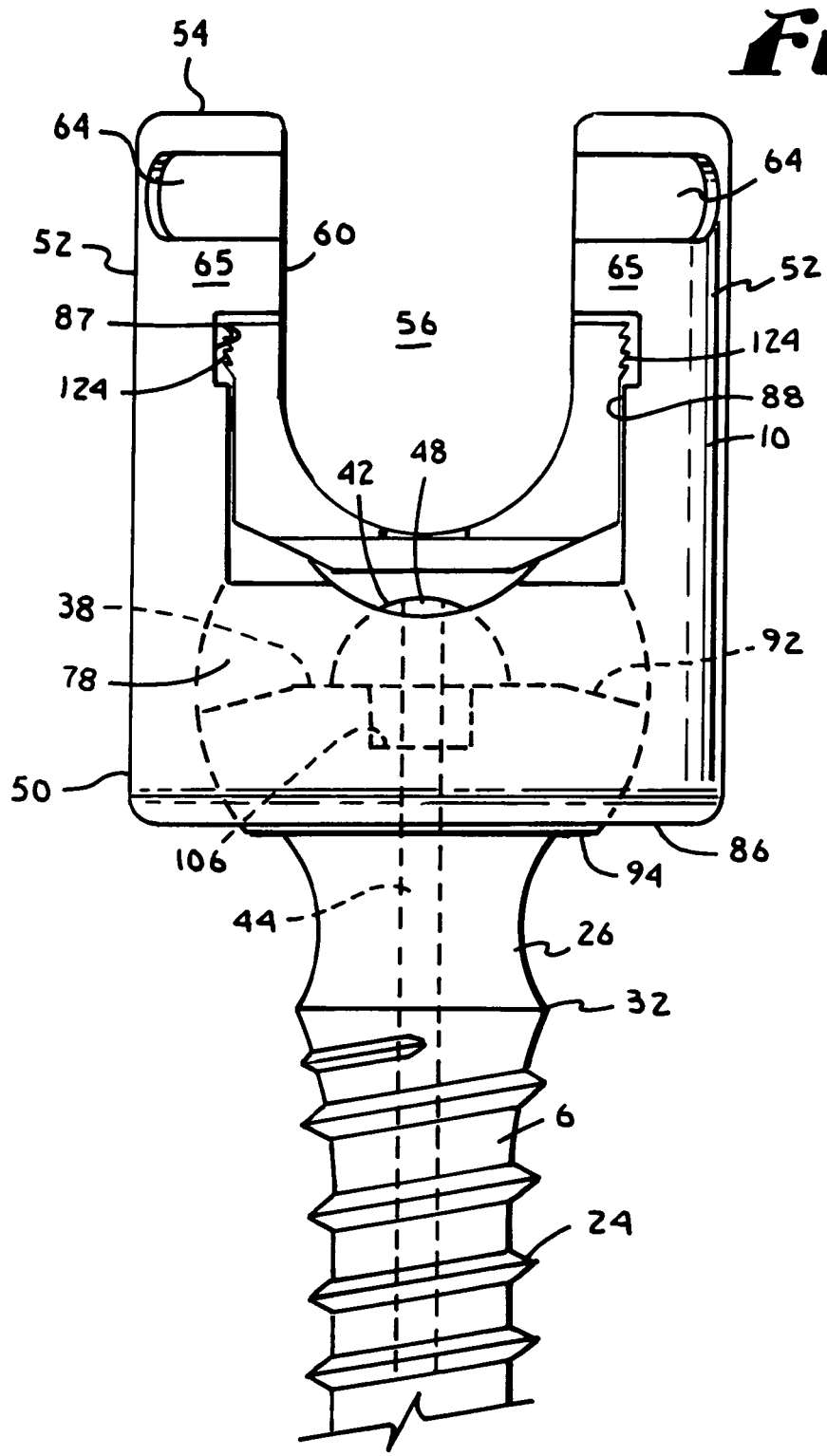
FIG. 10 is an enlarged and partial front elevational view of the assembly of FIG. 2.

On each arm 52, disposed adjacent to and directly below the guide and advancement structure 62 is an inner, inset surface 87 having a width or diameter greater than a distance between the interior surfaces 60 of the arms 52. An inner insert receiving surface 88 is located between the surface 87 and the inner substantially spherical surface 80. The insert receiving surface 88 includes a band of ridges or teeth 89 extending across each arm 52 and running parallel to the head top surface 54. The ridges or teeth 89 each incline in a downward direction toward the base 50 and are sized and shaped to cooperate with ratchet teeth disposed on the insert 14 as will be described more fully below. The inner surface 87 provides space for insertion of the insert 14 into the head 10 with no initial engagement of the teeth 89 with the head 10 as illustrated in FIG. 10.

The retaining and articulating structure or ring 12 is used to retain the capture structure 8 of the shank 4 within the head 10. The retaining and articulating structure 12, best illustrated by FIGS. 1, 14, 16 and 18, has an operational central axis that is the same as the elongate axis A associated with the shank 4, but when the retaining and articulating structure 12 is separated from the shank 4, the axis of rotation is identified as an axis C. The retaining and articulating structure 12 has a central bore 90 that passes entirely through the retaining and articulating structure 12 from a top surface 92 to a bottom surface 94 thereof. A first inner cylindrical surface 96 defines a substantial portion of the bore 90, the surface 96 having a helically wound guide and advancement structure thereon as shown by a helical rib or thread 98 extending from adjacent the top surface 92 to adjacent the bottom surface 94. Although a simple helical rib 98 is shown in the drawings, it is foreseen that other helical structures including other types of threads, such as buttress and reverse angle threads, and non threads, such as helically wound flanges with interlocking surfaces, may be alternatively used in an alternative embodiment of the present invention. The inner cylindrical surface 96 with helical rib 98 are configured to mate under rotation with the capture structure outer surface 34 and helical advancement structure or thread 36, as described more fully below.

The retaining and articulating structure 12 has a radially outer partially spherically shaped surface 104 sized and shaped to mate with the partial spherically shaped seating surface 82 of the head and having a radius approximately equal to the radius associated with the surface 82. The retaining and articulating structure radius is larger than the radius of the neck 83 of the head 10. Although not required, it is foreseen that the outer partially spherically shaped surfaced 104 may be a high friction surface such as a knurled surface or the like.

Figure 11:
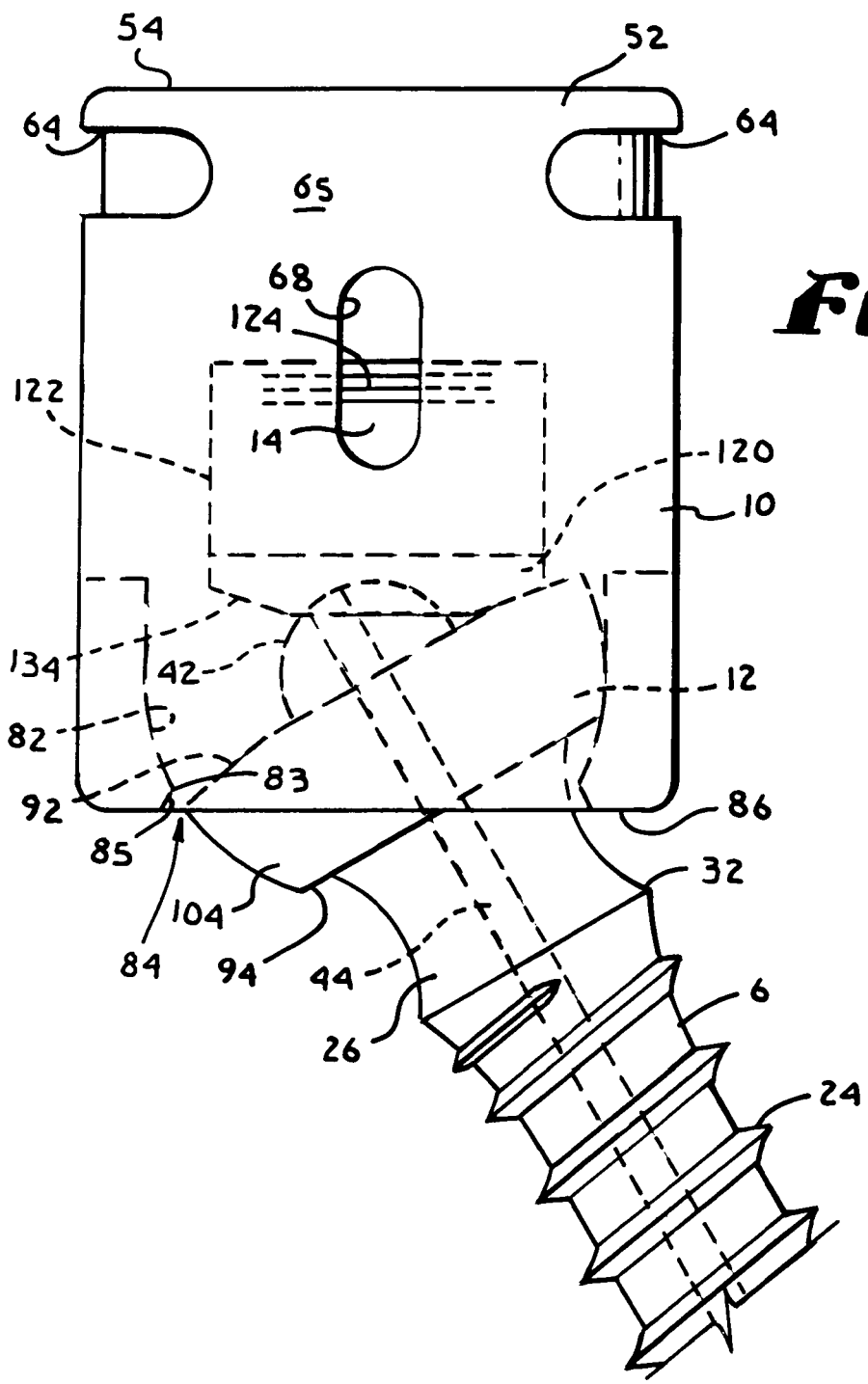
FIG. 11 is an enlarged and partial side elevational view of the assembly of FIG. 2 shown with the side-loading insert in engagement with the bone screw shank, setting the shank in an angle of articulation with respect to the head.
Figure 14:
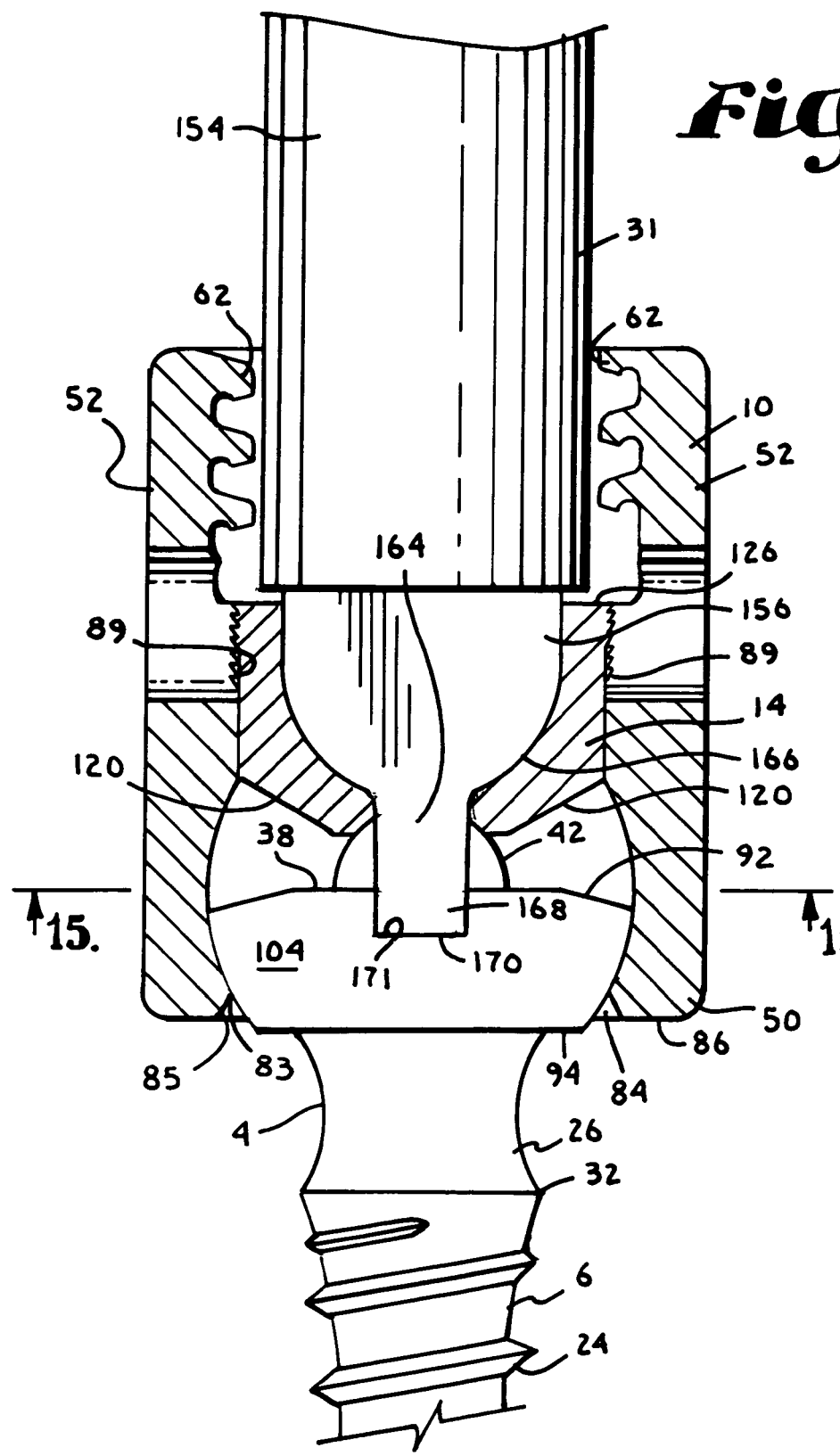
FIG. 14 is an enlarged and partial cross-sectional view of the head and insert taken along the line 14-14 of FIG. 2, shown with the shank and retaining and articulating structure in front elevation and further shown with the driving tool of FIG. 12.

The retaining and articulating structure top surface 92 extends from the central bore 90 to the outer surface 104. The top surface 92 is disposed at an angle with respect to the bottom surface 94, with the top surface 92 sloping in a downward direction toward the bottom surface 94 as the top surface 92 extends toward the outer surface 104. As illustrated in FIG. 11 and discussed more fully below, the angle of inclination of the top surface 92 is configured for contact and frictional engagement with a bottom surface of the insert 14.

The retaining and articulating structure 12 further includes a tool engagement structure in the form of a transverse slot 106 formed in the top surface 92 for engagement with the driving tool 31 shown in FIGS. 17 and 18. As will be described more fully below, the tool 31 is configured to fit within the transverse slot 106 on either side of the domed top 42 of the shank 4 and utilized for driving the shank body 6 into the vertebra 15.

The elongate rod or longitudinal member 21 that is utilized with the assembly 1 can be any of a variety of implants utilized in reconstructive spinal surgery, but is normally a cylindrical elongate structure having a smooth, outer cylindrical surface 108 of uniform diameter. The rod 21 is preferably sized and shaped to snugly seat near the bottom of the U-shaped channel 56 of the head 10 and, during normal operation, is positioned slightly above the bottom of the channel 56 at the lower seat 58. In the illustrated embodiment, the domed top 42 of the shank 4 does not come into direct contact with the rod 21, but rather, the side-loading insert 44 is received within the bone screw head 10 prior to rod insertion, and ultimately is positioned between the rod 21 and the top 42.

The insert 14 is best illustrated in FIGS. 3-7. The insert 14 includes a base 110 integral with a pair of upstanding arms 112. The base 110 and arms 112 form a generally U-shaped, open, through-channel 114 having a substantially cylindrical bottom seating surface 116 configured to operably snugly engage the rod 21. Each arm 112 has a faceted outer profile with a lower facet or face 120 extending from the base 110 and integral with a side facet or face 122 that includes a bar or rack of inclined teeth 124 for ratcheting the insert 14 down by degrees into the head 10 in cooperation with the ridges or teeth 89 disposed on the insert receiving surface 88, as will be described more fully below. Each side facet or face 122 extends between one of the lower facets 120 and a top surface 126. The ratchet teeth 124 are disposed near the top surface 126 and each tooth 124 runs in a direction parallel to the top surface 126. Furthermore, each tooth 124 includes a surface 130 inclined in an outward and upward direction toward the top surface 126. The teeth 124 are thus readily movable or ratcheted downwardly toward the cavity 78 of the bone screw head 10 when desired, after side insertion of the insert 14 into the head 10 as illustrated in FIGS. 1 and 2. Once the teeth 124 are pressed downwardly into engagement with the teeth 89, the insert 14 resists upward movement toward the opening 57 of the bone screw head channel 56.

Disposed on either side of each side facet 122 are lateral facets 128 that terminate at planar outer edge surfaces 132. Also extending between the edge surfaces 132 and the base 110 are lower facets 134. A pair of opposing, squared-off notches 136 are formed on each lower facet 134 in a central location where the facet 134 contacts the edge surfaces 132. The notches 136 are sized and shaped to correspond and cooperate with the transverse slot 106 of the retaining and articulating structure 12 to allow for insertion of the driving tool 31 through the notches 136 and into the slot 106 for engagement with the retaining and articulating structure during installation of the shank body 6 into bone.

Disposed centrally on a bottom surface 138 of the base 110, opposite the seating surface 116 is a concave, substantially spherical formation 140. A cannulation bore 142 extends through a central portion of the formation 140. The formation 140 is sized and shaped to snugly frictionally fit about the domed top 42 of the capture structure 8. As will be described in greater detail below, as the insert 14 is ratcheted downwardly into contact with the domed top 42 and the retaining and articulating structure 12, the insert 14 may be used to set the articulation of the shank body 6 with respect to the bone screw head 10 prior to insertion and locking of the rod 21 into the head 10, or by inserting and compressing the rod 21 with the closure top 18 and then releasing the closure top 18. As illustrated in FIG. 23 and discussed more fully below, the side bores or apertures 68 formed in the head 10 allow for manipulation of the insert 14 with respect to the dome shaped top 42 by a tool 146 that has opposed pinchers or prongs 147 for extending through the bores 68 and pressing against the arms 112 of the insert 14 to loosen the insert 14 from the head 10. Eventually, the rod 21 is placed in the U-shaped channel 56 and/or the rod 21 which has been placed in the channel directly, abutingly engages or re-engages the insert 14 that in turn engages the shank capture structure domed top 42, as shown, for example, in FIGS. 11 and 22, consequently biasing the shank 4 downwardly in a direction toward the base 50 of the head 10 when the assembly 1 is fully assembled. The shank 4 and retaining and articulating structure 12 are thereby locked in position relative to the head 10 by the rod 21 firmly pushing downward on the insert 14 and the shank domed top surface 42.

With reference to FIGS. 12-18, the driving tool 31 according to the invention includes a handle 150, an elongate cylindrical stem or shaft 154 and an engagement structure 156. The engagement structure 156 is configured to operably mate with both the insert 14 and the retaining and articulating structure 12 at the transverse slot 106 thereof. The shaft 154 with attached engagement structure 156 is receivable in and passes through the interior of the bone screw head 10. The stem or shaft 154 is rigidly attached to the handle 150 and coaxial therewith. The handle 150 includes outer grooves 158 disposed about an outer cylindrical surface 160 thereof to aid in gripping and rotating the respective components.

The engagement structure 156 includes an oblong support 162 with two opposed arms 164 extending downwardly from the support 162 and away from the shaft 154 at either end of the support 162. The oblong support 162 has a substantially cylindrical lower surface 166 sized and shaped to fit within the U-shaped channel 114 of the insert 14 and operably mate with the bottom seating surface 116 during turning rotation and driving the of the bone screw shank 4 into bone. Each arm 164 further includes an extension 168 sized and shaped to fit within the transverse slot 106 of the retaining and articulating structure 12. As illustrated in FIG. 16, each extension 168 has a thickness such that the extension 168 fits snugly between the threaded cylindrical surface 34 of the capture structure 8 and the inner surface 80 of the head 10, while a bottom surface 170 of the extension 168 seats evenly on a base surface 171 of the transverse slot 106. Each arm 164 also includes an inner seating surface 174 disposed parallel to the base surface 171. Each inner seating surface 174 is sized and shape to seat upon and engage the annular top surface 38 of the capture structure 8 when the extensions 168 are seated within the transverse slot 106. Thus, the engagement structure 156 of the driving tool 31 engages the bone screw assembly 1 at the lower cylindrical surface 166, the extensions 168 and the inner seating surface 174 when driving the shank body 6 into the vertebra 15, as will be described more fully below. The driving tool 31 also includes a centrally located cannulation bore 176 extending along a length thereof, sized shaped and located to cooperate with the cannulation bore 44 of the bone screw shank 4 and the cannulation bore 142 of the insert 14.

With particular reference to FIGS. 19-21, the closure structure or nested fastener 18 can be any of a variety of different types of closure structures for use in conjunction with the present invention with suitable mating structure on the upstanding arms 52 of the head 10. The fastener 18 screws between the spaced arms 52. The illustrated fastener 18 includes an outer fastener 204 and an uploaded set screw 206. The fastener 204 includes a base 208 integral or otherwise attached to a break-off head 210. The base 208 cooperates with the head 10 of the bone screw assembly 1, as illustrated in FIGS. 22-28, to close the head U-shaped channel 56 and to clamp the spinal fixation rod 21 within the bone screw head 10. The break-off installation head 210 includes a faceted outer surface 220 sized and shaped for engagement with a tool 221 for installing the fastener 204 to the bone screw head or receiver 10 and thereafter separating the break-off head 210 from a respective base 208 when installation torque exceeds selected levels.

The base 208 of the fastener 204 is substantially cylindrical, having an axis of rotation D and an external surface 250 having a guide and advancement structure 252 disposed thereon. The guide and advancement structure 252 is matingly attachable to the guide and advancement structure 62 of the bone screw head 10. As with the guide and advancement structure 62, the guide and advancement structure 252 can be of any type, including V-type threads, buttress threads, reverse angle threads, or square threads. Preferably the guide and advancement structure 252 is a helically wound flange form that interlocks with the reciprocal flange form as part of the guide and advancement structure 62 on the interior of the bone screw arms 52. The guide and advancement structures 62 and 252 are preferably of a type that do not exert radially outward forces on the arms 52 and thereby avoid tendencies toward splaying of the arms 52 of the bone screw head 10, when the fastener 204 is tightly torqued into the head 10.

The fastener 204 includes an internal, centrally located through-bore 254. At the base 208, the bore 254 is substantially defined by a guide and advancement structure, shown in FIGS. 20 and 21 as an internal V-shaped thread 256. The thread 256 is sized and shaped to receive the threaded set screw 206 therein as will be discussed in more detail below. Although a traditional V-shaped thread 256 is shown, it is foreseen that other types of helical guide and advancement structures may be used. Near a substantially annular planar top surface 258 of the base 208, an abutment shoulder 260, extends uniformly radially inwardly. The abutment shoulder 260 is spaced from the V-shaped thread 256 and sized and shaped to be a stop for the set screw 206, prohibiting the set screw 206 from advancing out of the top 258 of the base 208. It is foreseen that alternatively, the set screw 206 may be equipped with an outwardly extending abutment feature near a base thereof, with complimentary alterations made in the base 208, such that the set screw 206 would be prohibited from advancing out of the top 258 of the base 208 due to abutment of such outwardly extending feature against a surface of the base 208.

An inner cylindrical wall 262 separates the abutment shoulder 260 from the thread 256. The cylindrical wall 262 has a diameter slightly greater than a root or major diameter of the internal thread 256. The wall 262 partially defines a cylindrical space or passage 264 for axial adjustable placement of the screw 206 with respect to the rod 21 as will be discussed in more detail below.

The fastener 204 further includes the break-off head 210 that is integral or otherwise attached to the fastener 204 at a neck or weakened region 266. The neck 266 is dimensioned in thickness to control the torque at which the break-off head 210 separates from the fastener 204. The preselected separation torque of the neck 266 is designed to provide secure clamping of the rod 21 by the fastener 204 before the head 210 separates. For example, 120 inch pounds of force may be a selected break-off torque. The illustrated, hexagonal faceted surfaces 220 of the break-off head 210 enables positive, non-slip engagement of the head 210 by the installation and torquing tool 221 illustrated in FIG. 25. Separation of the break-off head 210 leaves only the more compact base 208 of the fastener 204 installed in the bone screw head or receiver 10, so that the installed fastener 204 has a low profile.

The base 208 of the fastener 204 may include structure to provide clamping engagement between the base 208 and the rod 21. In the embodiment disclosed in FIGS. 19-28, a bottom surface 268 of the base 208 has an interference structure in the form of a "cup point" or V-shaped ridge or ring 270. The V-ring 270 operably cuts into the outer surface 108 of the rod 21 during assembly, when the fastener 204 is threaded into the screw head 10, so that the fastener more positively secures the rod 21 against rotational and translational movement of the rod 21 relative to the bone screw head 10. As the rod 21 may be bent or skewed with respect to the head 10 at a location of engagement between the rod 21 and the fastener 204, only a portion or a side of the V-ring 270 may engage with and cut into the rod 21. It is also foreseen that in some embodiments, clamp enhancing structure on the fastener 204, such as the V-ring 270, or surface finish such as knurling, may or may not be necessary or desirable.

The uploadable set screw 206 has a substantially planar top 276 and a bottom 277. The set screw 206 is substantially cylindrical in shape, having an axis of rotation E, and includes an outer cylindrical surface 278 with a V-shaped thread 280 extending from the top 276 to the bottom 277 thereof. The surface 278 and thread 280 are sized and shaped to be received by and mated with the inner thread 256 of the fastener base 208 in a nested relationship. Thus, in operation, the axis of rotation E is the same as the axis of rotation D of the fastener 204.

The embodiment of the set screw 206 best illustrated in FIGS. 19-21 includes interference structure for enhancing clamping or setting engagement with the surface 108 of the rod 21. The bottom 277 of the illustrated set screw 206 has a centrally located set point 282 and a peripherally located cup point or V-shaped set ring 284 projecting therefrom. The set point 282 and the set ring 284 are designed to cut into the surface 108 of the rod 21 when the set screw 206 is tightly fastened into the fastener base 208. The set point 282 projects outwardly from the bottom 277 to a location beyond the outermost surface of the set ring 284. Thus, the set point 282 is an initial and primary source of engagement with the rod 21, directly pressing against the rod 18 along the central axis of rotation D of the set screw 206. As with the V-ring 270 of the fastener 204, the V-ring 284 may contact and press against the rod 21 only along a portion thereof if the rod 21 is bent or otherwise disposed in a skewed relationship with the bone screw head 10. It is foreseen that a domed shape projection (not shown) may be utilized in lieu of the set point 282. Such a projection may be a radially extending convex, curved, partially spherical or dome-shaped interference or compressive structure, having a substantially uniform radius to provide for positive engagement with the rod 21 at the surface 108. Such a domed structure may extend a greatest distance along the central axis E. It is also foreseen that other structures for enhancing clamping, such as knurling or the like may be used in some embodiments or none in others.

Figure 28:
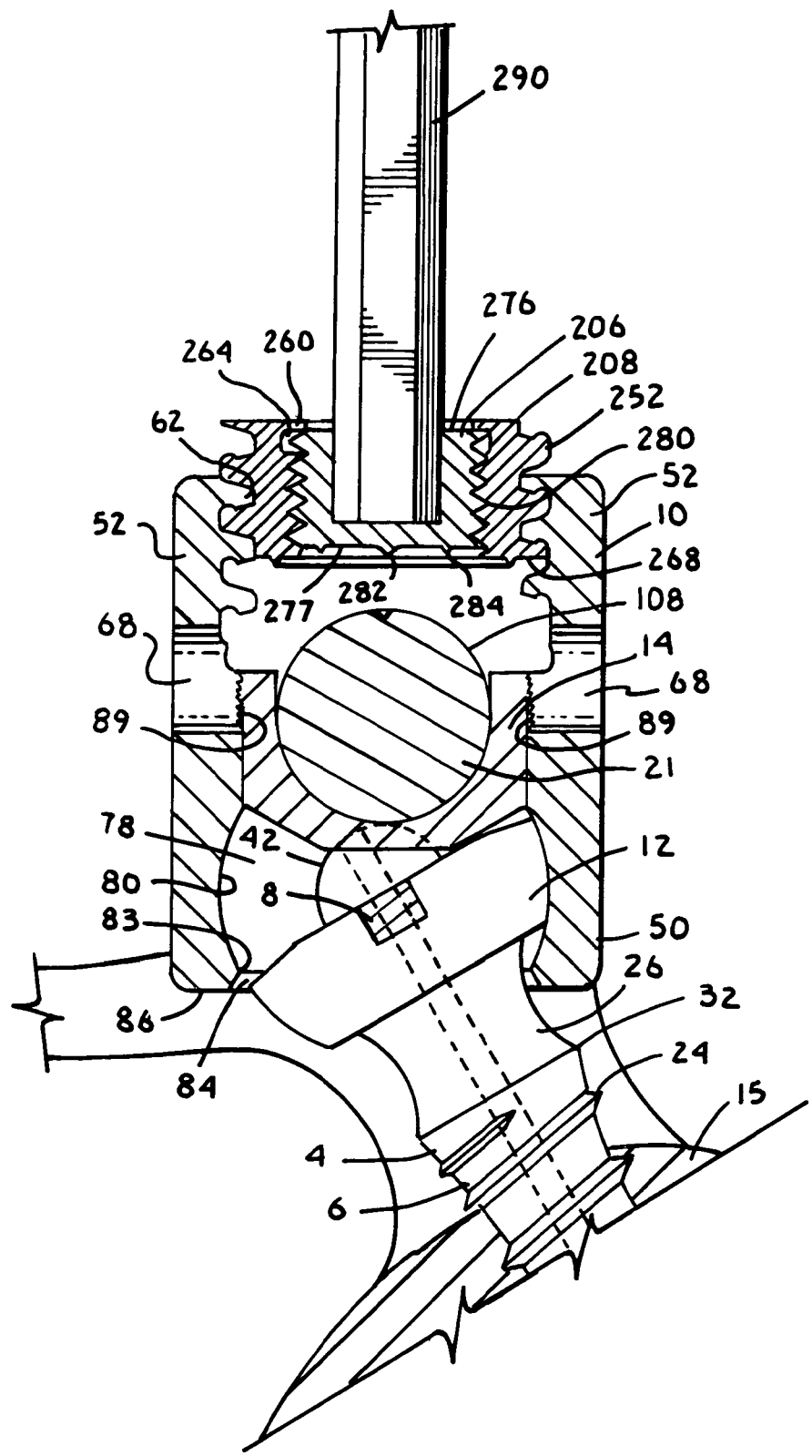
FIG. 28 is a partial cross-sectional view similar to FIG. 26, showing engagement and removal of the nested fastener from the bone screw head with a set screw tool.

The set screw 206 includes a central aperture 286 formed in the top 276 and defined by faceted side walls 288 and a hexagonal bottom seating surface 289, forming a hex-shaped internal drive for positive, non-slip engagement by a set screw installment and removal tool such as an Allen-type wrench 290 as depicted in FIGS. 20, 26 and 28. With reference to FIG. 20, the central aperture 286 cooperates with the central internal bore 254 of the fastener 204 for accessing and uploading the set screw 206 into the fastener 204 prior to engagement with the bone screw head 10. After the nested fastener 18 engages the bone screw head 10, and the break-off head 210 is broken off, the tool 290 is used to set and lock the set screw 206 against the rod 21 as illustrated in FIG. 26.

There are circumstances under which it is desirable or necessary to release the rod 21 from the bone screw head 10. For example, it might be necessary for a surgeon to re-adjust components of a spinal fixation system, including the rod 21, during an implant procedure, following an injury to a person with such a system implanted. In such circumstances, the tool 290 may be used to remove both the set screw 206 and attached fastener base 208 as a single unit, with the set screw 206 contacting and contained within the base 208 by the abutment shoulder 260. Thus, as illustrated in FIG. 28, rotation of the tool 290 engaged with the set screw 206 backs both the set screw 206 and the fastener base 208 out of the guide and advancement structure 252 in the arms 52 of the bone screw head 10, thereby releasing the rod 21 for removal from the bone screw head 10 or repositioning of the rod 21. It is foreseen that other removal structures such as side slots or other screw receiving and engagement structures may be used to engage the set screw 206 that is nested in the fastener base 208.

With reference to FIGS. 1 and 2, prior to the polyaxial bone screw assembly 1 being implanted in the vertebra 15, the retaining and articulating structure 12 is typically first inserted or top-loaded, into the head U-shaped channel 56, and then into the cavity 78 to dispose the structure 12 within the inner surface 80 of the head 10. The structure 12 is typically turned or rotated such that the axis C is perpendicular to the axis B of the head 10 during insertion of the structure 12 into the head 10. Then, after the retaining and articulating structure 12 is within the cavity 78, the retaining and articulating structure 12 is rotated approximately 90 degrees such that the axis C is coaxial with the axis B of the head 10, and then the structure 12 is seated in sliding engagement with the seating surface 82 of the head 10.

The shank capture structure 8 is preloaded, inserted or bottom-loaded into the head 10 through the bore 84 defined by the neck 83. In other embodiments according to the invention (not shown), the shank 4 may be sized and configured to be top-loaded, if desired in which case it must be inserted prior to the retaining and articulating structure 12. The retaining and articulating structure 12, now disposed in the head 10 is coaxially aligned with the shank capture structure 8 so that the helical v-shaped thread 36 rotatingly mates with the thread 98 of the retaining and articulating structure 12.

The shank 4 and/or the retaining and articulating structure 12 are rotated to fully mate the structures 36 and 98 along the respective cylindrical surfaces 34 and 96, fixing the capture structure 8 to the retaining and articulating structure 12, until the annular top surface 38 of the capture structure 8 and the retaining and articulating structure top surface 92 are contiguous. Permanent, rigid engagement of the capture structure 8 to the retaining and articulating structure 12 may be further ensured and supported by the use of adhesive, a spot weld, a one-way thread or deforming one or both of the threads 36 and 98 with a punch or the like.

With reference to FIG. 9, at this time the shank 4 is in slidable and rotatable engagement with respect to the head 10, while the capture structure 8 and the lower aperture or neck 83 of the head 10 cooperate to maintain the shank body 6 in rotational relation with the head 10. According to the embodiment of the invention shown in FIGS. 1-28, only the retaining and articulating structure 12 is in slidable engagement with the head spherical seating surface 82. Both the capture structure 8 and threaded portion of the shank body 6 are in spaced relation with the head 10. The shank body 6 can be rotated through a substantial angular rotation relative to the head 10, both from side to side and from front to rear so as to substantially provide a universal or ball joint wherein the angle of rotation is only restricted by engagement of the neck 26 of the shank body 6 with the neck or lower aperture 83 of the head 10. It is foreseen that in some embodiments that the retaining structure could simply keep the shank upper portion in the receiver and not articulate with the shank upper portion. In such embodiments, the shank upper portion could have a spherical enlargement that articulates with the head spherical seating surface, the insert and the retaining structure itself.

The insert 14 is then loaded into the head 10 as illustrated in FIGS. 1 and 2 and further operationally shown in FIGS. 9-11. With particular reference to FIG. 10, the insert U-shaped channel 114 is aligned with the head 10 U-shaped channel 56 and the insert 14 is initially side-loaded into the head 10 with the ratchet teeth 124 disposed adjacent to the surfaces 87 and directly above the ratchet teeth 89 of the insert receiving surface 88. Such placement allows for unrestricted angular rotation of the shank body 6 with respect to the head 10. As illustrated in FIG. 11, the insert 14 may be pushed downward into contact with the domed top 42, frictionally engaging the top 42 with the insert 14 and thus setting the angle of orientation of the shank body 6 with respect to the head 10 at any desired angle. Because of the orientation of the insert ratchet teeth 124 and the bone screw head ratchet teeth 89, the insert 14 is readily and easily pushed downward into the head and toward the domed top 42, setting or fixing the desired angle of orientation between the shank body 6 and the head 10. Again, this can be done directly with a tool or by compression through the rod 21. Furthermore, the cooperating ratchet teeth 124 and 89 resist any upward, loosening forces, as will be described more fully below. As shown in FIG. 11, a full range of articulation is possible utilizing the insert 14, also due to the cooperation of the sloped, faceted surfaces 120, 134, of the insert 14 and also the inclined top surface 92 of the retaining and articulating structure 12.

With reference to FIG. 10, and also FIGS. 12-18, the assembly 1 is typically screwed into a bone, such as the vertebra 15, by rotation of the shank 4 using the driving tool 31 that operably drives and rotates the shank 4 by engagement thereof with the insert 14 and the transverse slot 106 of the retaining and articulating structure 12. Specifically with reference to FIGS. 14-16, the tool 31 shown in FIGS. 12 and 13 is inserted into the head 10 of the bone screw fitted with an insert that has been loosely placed in the head 10 as shown in FIG. 10. The surface 166 of the driving tool 31 comes into contact with the bottom seating surface 116 of the insert 14 and the tool arms 164 extend through the insert notches 136, pushing the insert down into the head 10 until the tool extensions 168 seat within the transverse slot 106 with the tool bottom surface 170 frictionally engaging the base 171 defining the transverse slot 106. As illustrated in FIG. 16, some frictional engagement between the tool surface 174 and the top surface 38 of the capture structure 8 may also be achievable during rotation of the driving tool 31. It is foreseen that in other embodiments according to the invention, the transverse slot 106 may be replaced by other types of tool engaging recesses.

Preferably prior to implantation of the bone screw assembly 1 into the vertebra 15, the set screw 206 is assembled with the fastener 204. With particular reference to FIGS. 19-21, the Allen-type tool 290 is inserted through the bore 254 of the fastener 204 and into the aperture 286 of the set screw 206 until seated on the bottom surface 289, with faceted outer surfaces 292 of the tool 290 engaging the inner faceted walls 288 of the set screw 206. The set screw 206 is then uploaded into the fastener 204 by rotation of the set screw 206 with respect to the fastener 204 to mate the set screw thread 280 with the fastener inner thread 256 until the set screw top surface 276 abuts the abutment shoulder 260, resulting in the nested arrangement of the fastener 18 shown in FIG. 21, with the set screw 206 completely enveloped in the fastener base 208. The nested assembly 18 shown in FIG. 21 is now pre-assembled and ready for use with a bone screw head 10 and cooperating rod 21. As illustrated in FIG. 21, in such a pre-assembly arrangement, the V-ring 270 preferably projects beyond the point 282 and the V-ring 284 of the set screw 206, such that the base 208 will seat fully within the bone screw arms 52 prior to engagement of the set screw 206 with the rod 21.

Typically at least two and up to a plurality of bone screw assemblies 1 are implanted into vertebrae for use with the rod 21. With reference to FIGS. 17 and 18, each vertebra 15 may be pre-drilled to minimize stressing the bone and have the guide wire or pin 49 inserted therein that is shaped for the cannula 44 of the bone screw shank 6 and provides a guide for the placement and angle of the shank 4 with respect to the vertebra 15. A further tap hole may be made using a tap with the guide wire 49 as a guide. Then, the assembly 1 and the driving tool 31 are threaded onto the guide wire by first threading the wire into the bottom opening 46 of the shank body 6. The wire 49 is then threaded out of the top opening 48 and through the bore 142 of the insert 14 and then into the bore 176 of the driving tool 31. The shank body 6 is then driven into the vertebra 15, by rotation of the driving tool 31, using the wire 49 as a placement guide.

Figure 22:
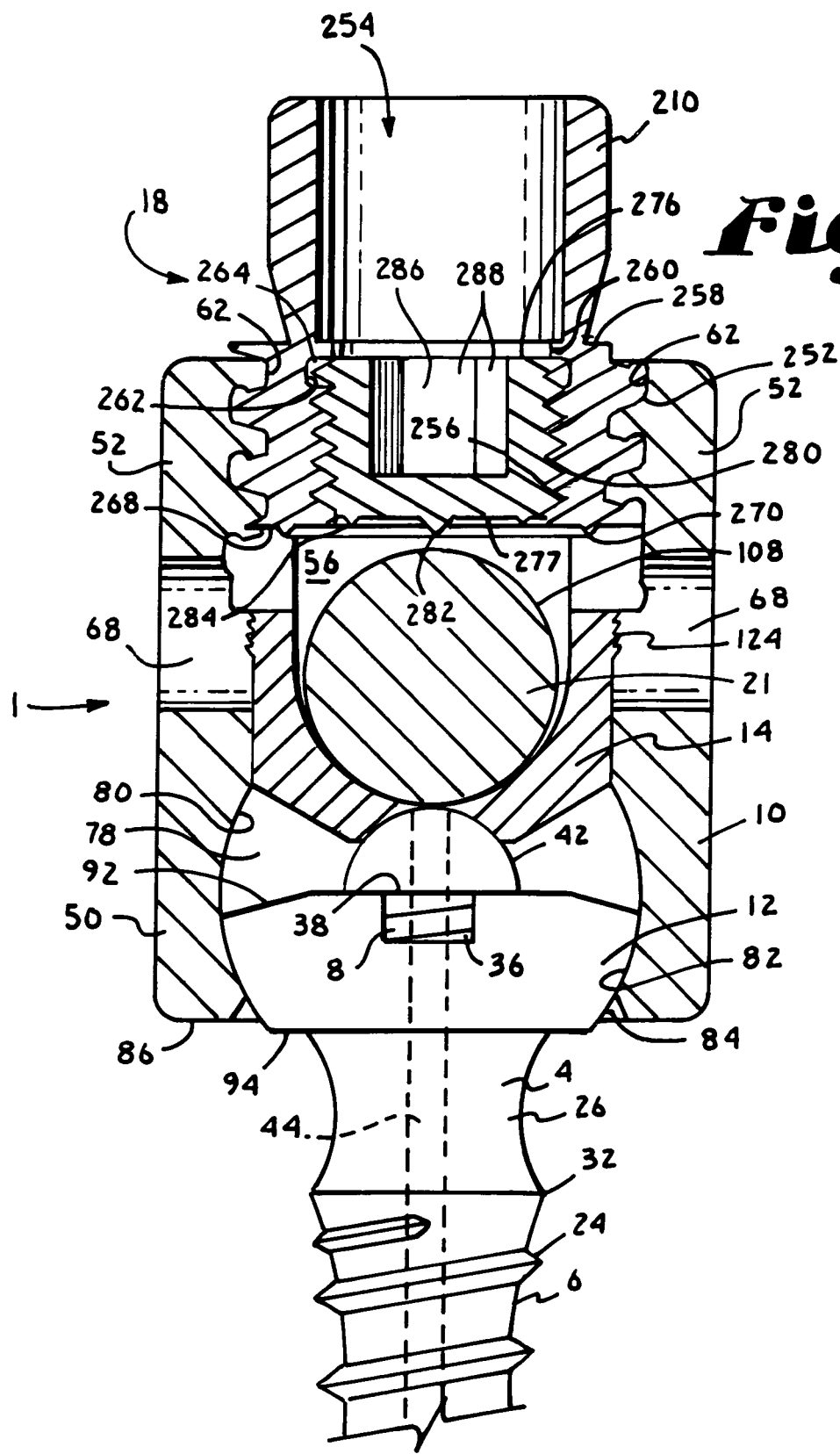
FIG. 22 is a partial cross-sectional view of the bone screw and insert assembly of FIG. 14 shown with a rod, also in cross-section and in a process of mating with the nested bone screw fastener assembly of FIG. 21.
Figure 23:
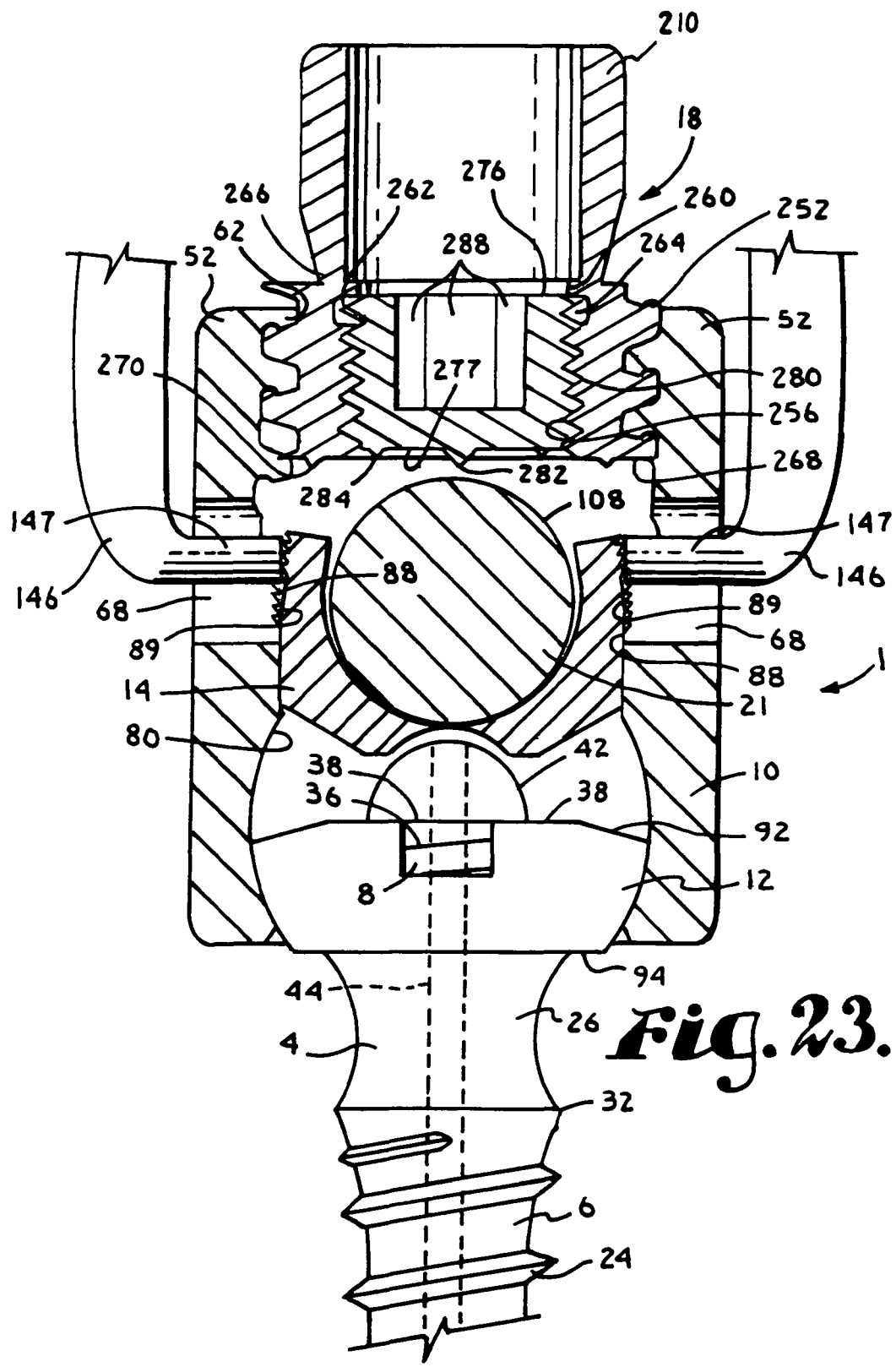
FIG. 23 is a partial cross-sectional view, similar to FIG. 22 shown with a manipulation tool in a process of moving the side-loaded insert upwardly and away from the bone screw shank to allow for pivoting of the bone screw shank with respect to the head.

With reference to FIG. 22, the rod 21 is eventually positioned within the head U-shaped channel 56, and the nested fastener 18 is then inserted into and advanced between the arms 52. With reference to FIG. 23, before or after rod insertion, it may be desirable to move the insert 14 to a position disengaged from the shank domed top 42 to allow for rotation of the shank body 6 with respect to the head 10 to a desired angle of articulation. As illustrated in FIG. 23, the manipulation tool 146 may be utilized for such purpose by inserting the prongs 147 of the tool 146 into the opposing bores 68 and pinching or squeezing the insert arms 112 toward one another to release the insert ratchet teeth 124 from the ratchet teeth 89 disposed on the head 10, and then move the insert 14 up and away from the domed top 42. The tool 146 may also be used to lower the insert 14 into position against the domed top 42. The bores 68 are preferably configured with an oblong orientation such that the insert 14 may be accessed for upward and downward positioning. Thus, utilizing the insert 14, a bone screw assembly 1 may be set and fixed at a desired angle of articulation prior to implantation of the rod 21, or after the rod 21 is placed in the head 10. Furthermore, if it is desired for the bone screw shank to remain rotatable with respect to the head 10 during part or all of a procedure until the rod 21 and bone screw assembly 1 are clamped into final position with the fastener 18, the insert 14 may be manipulated as shown in FIG. 23 to provide for such freedom of articulation.

With reference to FIG. 24, the insert 14 is pressed downwardly into engagement with the shank domed top surface 42 to set the angle of articulation of the shank body 6 with respect to the head 10 at the position shown. The rod 21 is seated on the insert 14 and the fastener 18 is initially placed between the arms 52 and rotated using the installation tool 221 engaged with the surfaces 220 of the break-off head 210 until the fastener guide and advancement structure 252 is fully mated with the head guide and advancement structure 62, but with the set screw 206 in position within the fastener base 208 such that the point 282 and the ring 284 are not engaged with the rod 21. With reference to FIG. 25, the break-off head 210 is then twisted to a preselected torque, for example 90 to 120 inch pounds, also utilizing the tool 221 in engagement with the faceted outer surface 220 of the break-off head 210, with or without bending of the rod 21 in order to achieve and maintain a desired alignment of the spine.

With reference to FIGS. 26 and 27, thereafter, the set screws 206 are tightened, preferably in a selected order, by inserting the Allen-type tool 290 into the aperture 286 and rotating the tool 290 to thread the set screw 206 downwardly toward the rod 21. As each set screw 206 is torqued tightly using the tool 290, first the point 282 and then portions of the V-ring 284 preferably come into contact and abrade or dig into the rod surface 108.

As previously discussed herein, because the rod 21 may be bent, not all projected portions of the fastener base 208 and the set screw 206 may come into contact with the rod 21. The availability of multiple locations of engagement of the fastener base 208 and the set screw 206 with the rod 21 increases the probability that the rod 21 will be engaged securely by the nested fastener assembly 18. It is noted that the fastener base 208 may only seat at the bottom of the bone screw head opening 57 so as to close the opening 57 and capture the rod 21 therein without the V-ring 270 or the base 268 contacting the rod surface 108. The set screw 206 is then turned and tightened against the rod 21, the point 284 engaging the rod surface 108 and thereby securing the rod 21 in place.

FIG. 27 illustrates the polyaxial bone screw assembly 1 and including the rod 21 and the nested fastener 18 positioned in a vertebra 15. The axis A of the bone shank 4 is illustrated as not being coaxial with the axis B of the head 10 and the shank 4 is fixed in this angular locked configuration. Other angular configurations can be achieved, as required during installation surgery due to positioning of the rod 21 or the like. It is noted that in the illustrated embodiment, the shank domed top 42 is rounded to approximately equally extend upward into the channel 56 approximately the same amount no matter what degree of rotation exists between the shank 4 and head 10 and the surface 42 is sized to extend slightly upwardly into the U-shaped channel 56. Thus, the surface 42 is engaged by the insert 14 that is in turn engaged by the rod 21 and pushed downwardly toward the base 50 of the head 10 when the nested fastener 18 biases downwardly toward and onto the rod 21. However, it is foreseen that the thickness of the insert 14 may be increased to allow for a shank top that does not extend into the U-shaped channel 56.

The downward pressure on the shank 4 pressed upon by the insert 14 in turn urges the retaining and articulating structure 12 downward toward the head seating surface 82, with the retaining and articulating structure outer surface 104 in frictional engagement with the head seating surface 82. As the nested fastener 18 presses against the rod 21, the rod 21 presses against the shank and the retaining and articulating structure 12 that is now rigidly attached to the shank 4 which in turn becomes frictionally and rigidly attached to the head 10, fixing the shank body 6 in a desired angular configuration with respect to the head 10 and the rod 21.

With reference to FIG. 28, if removal of the assembly 1 is necessary, or if it is desired to release the rod 21 at a particular location, disassembly is accomplished by using the Allen-type driving tool 290, mated with the set screw 206 at the aperture 286 and turned in a direction to rotate the set screw 206 up and out of the base 208. The set screw top 276 then backs into and abuts the abutment shoulder 260, transferring rotational torque exerted from the tool 290 from the set screw 206 to the fastener base 208. The base 208 then rotates with the guide and advancement structure 252 threading out of the guide and advancement structure 62 of the head 10. Thus, both the set screw 206 and the fastener base 208 are removed from the bone screw head 10 at the same time. If desired, the manipulation tool 146 may be used as shown in FIG. 23 and previously described herein to disengage the insert 14 from the shank domed top 42. Finally, disassembly of the assembly 1 is accomplished in reverse order to the procedure described previously herein for assembly.

With reference to FIGS. 29-42, the reference number 301 generally represents a second or alternative embodiment of an assembly according to the present invention. The assembly 301 includes a bone screw shank 304, having a capture structure 306 and a shank body 308 with a thread 310 for threadably implanting into a bone, such as a vertebra 313, and a head or receiver 314 which connects with the shank 304 to engage and secure a structural member, such as a spinal fixation rod 316, relative to the vertebra 313. The assembly 301 also includes a retaining and articulating structure or ring 320 operably positioned within the head or receiver 314 and engaging the capture structure 306 on the upper portion of the shank 304. The capture structure 306 is retained within the head or receiver 314 by the retaining and articulating structure 320 as will be described more fully below. The assembly 301 further includes a pressure insert 324, engageable with the upper portion of the capture structure 306 and the rod 316 as will be described more fully below. The shank 304, head or receiver 314, retaining and articulating structure 320 and the insert 324 are preferably assembled prior to implantation of the shank body 308 into the vertebra 313.

With reference to FIG. 42, the assembly 301 further includes a closure top 326 for fixing the rod 316 within the head or receiver 314. The insert 324 allows for setting an angle of articulation between the shank body 308 and the head or receiver 314 prior to insertion of the rod 316, if desired. Upon installation, which will be described in detail below, the closure top 326 presses against the rod 316 that in turn presses against the insert 324 that presses against the upper end of the capture structure 306 which biases the retaining and articulating structure 320 into fixed frictional contact with the head or receiver 314, so as to fix the rod 316 relative to the vertebra 313. The head or receiver 314 and shank 304 cooperate in such a manner that the head or receiver 314 and shank 304 can be secured at any of a plurality of angles, articulations or rotational alignments relative to one another and within a selected range of angles both from side to side and from front to rear, to enable flexible or articulated engagement of the head or receiver 314 with the shank 304 until both are locked or fixed relative to each other.

Referring to FIGS. 29, 36-38 and 40, the shank 304 is elongated and sized and shaped to be screwed into one of the vertebra 313. The shank body 308 includes the external helically wound thread 310 that extends from an outer tip 330 to a neck 332 disposed adjacent the capture structure 306.

On the illustrated shank 304, the capture structure 306 includes a region 334 that is frusto-conical in shape, diverging in diameter in a direction away from the outer tip 330 and that is coaxially aligned with an axis of rotation of the shank body 308. The region 334 terminates at an annular seating surface 335. The illustrated capture structure 306 has a maximum radius that is less than a radius associated with the shank thread 310 and further, preferably less than the radius of the shank body 308 whereupon the thread 8 is located.

The capture structure 306 has a plurality of tool engageable grooves, apertures or the like 336 to enable positive engagement by an appropriately shaped installation tool 338 to thread and drive the shank body 308 into the vertebra 313 as will be discussed in greater detail below. The illustrated shank capture structure 306 includes four evenly spaced tool engageable grooves 336, but it is foreseen that the driving structure may include fewer grooves, an alternative configuration of grooves or other driver receiving structure. An upper end surface 340 of the capture structure 306 opposite the tip 330 is provided with a formation or dome 342 to be positively and interferingly engaged by the insert 324, which in turn is positively engaged by the rod 316 when the assembly 301 is assembled into place. The illustrated dome 342 is radiused, knurled and centered on the upper end surface 340 so as to be coaxial with the remainder of the shank 304. The scoring or knurling of the dome 342 operably frictionally abuts against the insert 324 when the insert 324 is rotated into engagement with the head or receiver 314, as described more fully below, to provide for a selected setting of a desired angle of articulation between the shank body 308 and the head 314 prior to insertion and locking down of the rod 315. It is foreseen that in certain embodiments, the purpose of the dome 342 is simply to be engaged by the insert 324 that is in turn engaged by the rod 316, pushing the shank 304 in such a manner as to frictionally engage the retaining and articulating structure 320 with the head 314 as described below. Preferably, the dome 342 is radiused so that the dome 342 engages the insert 324 at approximately the same location regardless of the angle of articulation of the shank body 308 with respect to the head 314. However, it is foreseen that in certain embodiments shapes other than the dome 342 could be utilized.

Referring to FIGS. 29-31, and 36-42, the head or receiver 314 is generally cylindrical in external profile and has a central and axially aligned shank receiving bore 346 ending at an inner and lower neck 347. The neck 347 is radiused to receive the shank capture structure 306 and preferably smaller than a radius of the shank body 308 and thread 310. The bore 346 is also preferably sized larger than the capture structure 306 of the shank 304 to enable the shank 394 to be oriented through a range of angular dispositions relative to the head or receiver 314. The bore 346 may be conically counterbored or beveled in a region 348 to widen the angular range of the shank 304.

The head or receiver 314 is provided with a U-shaped rod cradle 350 sized to receive the rod 316 therethrough. The illustrated cradle 350 is rounded and radiused at an inner or lower portion or seat 352 to snugly mate with a cylindrical outer surface 354 of the rod 316 and open at an outer end or top 356, with spaced apart side surfaces 358 so as to form upstanding and spaced apart arms 360. The side surfaces 358 have guide and advancement structures 362 formed thereon that are complementary to guide and advancement structures 364 of the closure top 326 (FIG. 42). The illustrated structures 362 and 364 are helically wound flanges or threads that advance the closure top 326 into the head 314, as the closure top 326 is rotated about a central axis thereof. It is foreseen that the structures 362 and 364 may be interlocking helical flange forms similar to the structures 62 and 252 previously described herein with respect to the assembly 1, V-shaped threads, buttress threads, square threads, reverse angle threads, or other types of threads or flange forms. Preferably, the structures 362 and 364 are of such a nature as to resist splaying of the arms 360 when the closure top 326 is advanced into the U-shaped cradle 350.

Furthermore the head or receiver 314 includes an assembly cavity 366 formed therein that opens into the cradle 350. A partially spherical socket or seat 368 defines the assembly cavity 366. The seat 368 is disposed between the arm inner surfaces 358 and the neck 347 defining the shank bore 346 and as illustrated has a radius that is slightly less than a radius of the assembly cavity 366. The seat 368 has a substantially spherical shape and extends upward coaxially through the head 314 from the neck 347 to the cavity 366. The cavity 366 and the seat 368 will be detailed further below.

Each arm inner surface 358 further includes a recessed portion 370 disposed between the guide and advancement structure 362 and the seat 368. The portion 370 is defined by an upper shoulder 372, a lower shoulder 374 and a wall 376 disposed between the upper and lower shoulders 372, 374. The wall 376 is parallel to an axis of rotation of the head 314 that is operably coaxial with the shank 304. As will be described in greater detail below, the insert 324 may be operably disposed in the recessed portion 370 and include a setting position wherein the insert 324 abuts against the upper shoulder 372 and presses against the shank capture structure dome 342, allowing for the setting of a desired angle of articulation of the bone screw shank body 308 with respect to the head 314 during surgery, prior to lock down of the rod 316 by the closure top 326. The head or receiver 314 may further include external, closed end grip bores 378 for positive engagement by a holding tool (not shown) to facilitate secure gripping of the head 314 during assembly, installation and/or manipulation of the assembly 301.

The retaining and articulating structure 320, best illustrated in FIGS. 29-31 and 36 is used to retain the capture structure 306 within the head or receiver 314. The retaining and articulating structure 320 is in the form of a discontinuous ring that resiliently expands and contracts to enable the structure 320 to be snapped over and seated on the capture structure 306. The retaining and articulating structure 320, similar to a remainder of the assembly 301, is preferably formed of a material such as a spring stainless steel, tantalum, titanium or other resilient implantable material. The illustrated retaining and articulating structure 320 forms a gap or radial split 380 extending from a top surface 382 to a bottom surface 384 thereof, that allows the structure 320 to expand in circumference to fit over the capture structure 306. The retaining and articulating structure 320 includes an inner surface 382 formed by a through-bore sized and shaped to be compatible with the conical shape of the capture structure 306. The retaining and articulating structure 320 has an outer surface that is frusto-spherical, partially spherical, or a segment of a sphere, with a spherical radius approximately equivalent to the spherical radius of the spherical seat 368 within the head 314 and smaller than a radius of the cavity 366. As will be described more fully below, the bottom surface 384 seats upon the annular seating surface 335 of the shank capture structure 306 when the retaining and articulating structure 320 is fully installed on the capture structure 306.

The closure top 326 is generally cylindrical in shape and is provided with a break-off head 390 that is connected to the closure top 326 by a weakened area or neck 392 such that the break-off head 390 separates from the closure top 326 at a predetermined torque applied to the break-off head 390 during assembly. The illustrated break-off head 390 has a hexagonal cross section for engagement by a tool (not shown) of a complementary shape. The closure top 326 further includes a central point 394 for abrading and/or penetrating the rod 316 when fully installed on the head 314. Furthermore, the closure top 326 includes a driving formation, such as a hex aperture (not shown) for removal of the closure top, if desired, after the break-off head 390 is broken off.

The insert 324 is best illustrated in FIGS. 32-35. The insert 324 includes a substantially conical base portion 401 integral with a body portion 404. The base portion 401 extends outwardly from an annular, flat bottom surface 402 to the body portion 404. The body portion 404 is oblong, having a width W that is smaller than a length L thereof. The width W is bounded by two substantially flat surfaces 405. The width W is slightly smaller than a distance between the inner surfaces of the arms 358 of the head 314. The length L, taken along a center line 406 is slightly smaller than a diameter of the recessed portion 370 measured between the surfaces 376. A U-shaped cradle or channel 407 running parallel to the width W extends through the body portion 404, and is sized and shaped to receive the rod 316 thereon as will be described more fully below. Arms 408 disposed on either side of the cradle 406 each included a top surface 410 that is parallel to the bottom surface 402 and a sloped surface 412, starting at the top surface 410 and sloping downwardly toward the base portion 401. The arms 408 also include rounded, substantially cylindrical side surfaces 414, each having a radius slightly smaller than a radius of the wall 376 that partially defines the recessed portion 370 of the head 314. The sloped surfaces 412 are disposed opposite one another and the top surfaces 410 are disposed opposite one another. The sloped surfaces 412 also slope in opposite directions, each starting at the center line or axis 406 and running outwardly and downwardly away therefrom to provide for a cam action when the insert 324 is placed in the head 314 as shown in FIG. 37, and then rotated, the sloped surfaces 412 engaging the upper shoulder 372 of the recessed portion 370 of the head 314 and thus transforming the circular motion of rotating the insert 324 in the recessed portion 370 of the head 314 into linear motion, pressing the insert 324 against the shank dome 342 as will be described more fully below.

Each arm 408 of the body portion 404 includes a substantially flat bottom surface 416 extending from the conical base portion 401 to the cylindrical surface 414. The base portion 401 further includes a centrally located concave, substantially spherical bottom formation 418 contiguous to the annular bottom surface 402. The spherical bottom formation 418 is sized and shaped to cooperate and engage with the dome 342 of the shank capture structure 306, providing a snug, frictional fit. Apertures 420 extend through the U-shaped cradle 407 and are sized and shaped to cooperate and align with the apertures 336 of the capture structure 306. Thus, in the illustrated embodiment, four evenly spaced apertures 420 extend through the insert 324 and axially align with the apertures 336 as illustrated in FIGS. 39 and 40, both when the insert 324 is initially placed in the head 314 and when the insert 324 is rotated within the head 314 such that the top surfaces 410 are adjacent the upper shoulder 371. Alignment of the apertures 420 and the apertures 336 allow for engagement between the capture structure 306, the insert 324 and the driving tool 338 as will be described more fully below.

The driver 338 illustrated at FIG. 40 includes a handle (not shown), a drive shaft 426 and an engagement portion 428. The engagement portion 426 includes an oblong support 430 sized and shaped to fit within the U-shaped cradle 407 of the insert 324. Four prongs 432 extending from the oblong support 430 are sized and shaped to extend through the apertures 420 of the insert 324 and into the apertures 336 in the capture structure 306, thus operably engaging both the bone screw shank 304 and the insert 324 when rotating and driving the shank body 308 into the vertebra 313.

FIGS. 30, 31 and 36 illustrate the assembly of the bone screw head 314, shank 304 and retaining and articulating structure 320. In FIG. 30, the retaining and articulating structure 320 is inserted into the head 314 through an interior of the U-shaped cradle 350. The retaining and articulating structure 320 is first oriented with a central axis thereof at a right angle to a central axis of the bore 346. Then, the retaining and articulating structure is oriented as illustrated in FIG. 31 with the central axis of the retaining and articulating structure 320 being parallel or coincident with the axis of the bore 346 and the neck 347, by rotating the retaining and articulating structure 320 within the assembly cavity 366. With reference to FIG. 36, the capture structure 306 of the shank 304 is then inserted through the head bore 346 and then adjacent to the retaining and articulating structure inner surface 386 by expanding the retaining and articulating structure 320 at the radial split 380 so as to snap the retaining and articulating structure 320 over and around the capture structure 306 at the frusto-conical surface 334. The relative resistance encountered by the retaining and articulating structure 320 allows the capture structure 306 to expand the circumference of the retaining and articulating structure 320, by expansion of the split 380, so that the capture structure 306 enters the retaining and articulating structure 320. As illustrated in FIG. 37, when fully seated, the surface 334 frictionally engages the retaining and articulating structure inner surface 386 and the bottom surface 384 of the retaining and articulating structure 320 abuts against the annular seating surface 335 of the capture structure 306 thereby limiting penetration of the capture structure 306 into the retaining and articulating ring structure 320.

FIG. 37 shows the assembly 301 with the retaining and articulating structure 320 lowered from the assembly position and positioned in the spherical seat 368 with the central axis of the shank 304 coaxial with the central axis of the head 314. However, similar to the assembly 1, the relevant discussion of which is incorporated by reference herein, the curved or spherical seat 368 and the curved or spherical outer surface 388 of the retaining and articulating structure 320, allows universal angular positioning of the shank 304 relative to the head 314. The retaining and articulating structure 320, thus performs the functions of preventing the capture structure 306 of the shank 304 from slipping through the neck 347 and, in conjunction with the seat 368, forms a ball joint for relative orientation of the shank 304 and the head 314.

The insert 324 is then loaded into the head 314 as illustrated in FIGS. 37 and 39, with the width dimension W being oriented as shown with respect to the arms 360 to allow top loading of the insert 324. The insert 324 is lowered into the head 314 until the concave bottom formation 418 is seated on the dome 342.

For driving the bone screw shank body 308 into bone, such as the vertebra 313, the insert 324 is first rotated axially as illustrated in FIGS. 40 and 41, with the sloping surfaces 412 of the insert 324 contacting the upper shoulder 372 defining the head recessed portion 370, thereby pushing the capture structure 306 and attached retaining and articulating structure 320 downwardly against the seat 368. As the insert is rotated approximately 90 degrees until the flat surfaces 410 fully engage the upper shoulder 372, the insert 324 functions as a cam, providing a mechanical linkage that converts rotary motion to linear motion. Frictional engagement between the retaining and articulating structure 320 and the seat 368 sets the bone shank 304 in an angular position with respect to the head 314, but does not lock such into position. Thus, the insert 324 may be used at any time during a procedure to set the shank body 308 at a desired angle with respect to the head 314, but that position is not rigidly fixed until the rod 316 presses down upon the insert 324. When the insert flat surfaces 410 engage the upper shoulder 372, the apertures 420 of the insert 324 are aligned with the apertures 336 of the capture structure 306 and the insert cradle 407 is oriented in a position to receive the oblong support 430 of the driving tool engagement portion 428.

With particular reference to FIG. 40, the assembly 301 is typically screwed into a bone, such as the vertebra 313, by rotation of the shank 304 using the driving tool 338 that operably drives and rotates the shank 304 by engagement thereof with the insert 324 and the apertures 336 of the capture structure 306. The driving tool 338 is inserted into the head 314 of the bone screw with the prongs 432 first inserted into the apertures 420 and then the apertures 336 until the oblong support 430 is seated on the insert cradle 407.

Typically at least two and up to a plurality of bone screw assemblies 301 are implanted into vertebrae for use with the rod 316. As described with respect to the assembly 1, and incorporated by reference herein, each vertebra 313 may be pre-drilled to minimize stressing the bone. Although not shown, the assembly 301 may be cannulated in a manner as described with respect to the assembly 1 so that a guide wire or pin may be used as a guide for the placement and angle of the assembly 301. The shank body 308 is then driven into the vertebra 313, by rotation of the driving tool 338.

With reference to FIG. 42, the rod 316 is eventually positioned within the head U-shaped rod cradle 350, and the closure top 326 is then inserted into and advanced between the arms 360. Before rod insertion, it may be desirable to rotate the insert 324 to a position disengaged from the shank domed top 342 as shown in FIG. 37, to allow for a loose angular connection of the shank body 308 with respect to the head 314 until a desired angle of articulation is decided upon. The driving tool 338 may be utilized to rotate the insert 324 by inserting the prongs 432 in the apertures 420. Then, the insert 324 may be rotated to the position shown in FIG. 41, setting, but not locking such desired angular orientation between the shank body 308 and the head 314. In other words, when the insert 324 is in contact with the upper shoulder 372, the insert 324 presses down on the shank 304, providing sufficient frictional engagement between the retaining and articulating structure 320 and the head seat 368 that the shank 304 resists angular movement. However, it may not be desirable to rotate the insert 324 in order to change the angular orientation of the shank 304 with respect to the head 314. The shank 304 may simply be moved, using some force, to a desired position, which will then be the set position.

With reference to FIG. 24, the rod 316 is seated on the insert 324 and the closure top 326 is initially placed between the arms 360 and rotated using an installation tool (not shown) engaged with surfaces of the break-off head 390 until the guide and advancement structure 364 is fully mated with the head guide and advancement structure 262, with the point 394 penetrating the rod 316. The break-off head 390 is then twisted to a preselected torque, for example 90 to 120 inch pounds, until broken off.

If removal of the assembly 301 is necessary, or if it is desired to release the rod 316 at a particular location, disassembly is accomplished by using a tool (not shown) with a driving formation (not shown) located on the closure top 326 to rotate and remove the closure top 326 from the head 314. Disassembly of the assembly 301 is accomplished in reverse order to the procedure described previously herein for assembly.

With reference to FIGS. 43-54, the reference number 501 generally represents a third embodiment of an assembly according to the present invention. The assembly 401 includes a bone screw shank 504, having a capture structure 506 and a shank body 508 with a thread 510 for threadably implanting into a bone, such as a vertebra 513, and a head or receiver 514 which connects with the shank 504 to engage and secure a structural member, such as a spinal fixation rod 516, relative to the vertebra 513. The assembly 501 also includes a retaining and articulating structure or ring 520 operably positioned within the head or receiver 514 and engaging the capture structure 506 of the shank 504. The capture structure 506 is retained within the head or receiver 514 by the retaining and articulating structure 520 as will be described more fully below. The assembly 501 further includes a pressure insert 524, engageable with the capture structure 506 and the rod 516 as will be described more fully below. The shank 504, head or receiver 514, retaining and articulating structure 520 and the insert 524 are preferably assembled prior to implantation of the shank body 508 into the vertebra 513.

With reference to FIG. 54, the assembly 501 further includes a closure top 526 for fixing the rod 516 within the head or receiver 514. The insert 524 allows for setting an angle of articulation between the shank body 508 and the head or receiver 514 prior to insertion of the rod 516, if desired. Upon installation, which will be described in detail below, the closure top 526 presses against the rod 516 that in turn presses against the insert 524 that presses against the capture structure 506 which biases the retaining and articulating structure 520 into fixed frictional contact with the head or receiver 514, so as to fix the rod 516 relative to the vertebra 513. The head or receiver 514 and shank 504 cooperate in such a manner that the head or receiver 514 and shank 504 can be secured at any of a plurality of angles, articulations or rotational alignments relative to one another and within a selected range of angles both from side to side and from front to rear, to enable flexible or articulated engagement of the head or receiver 514 with the shank 504 until both are locked or fixed relative to each other.

Referring to FIGS. 43, 46-48 and 52, the shank 504 is elongated and sized and shaped to be screwed into one of the vertebra 513. The shank body 508 includes the external helically wound thread 510 that extends from an outer tip 530 to a neck 532 disposed adjacent the capture structure 506.

On the illustrated shank 504, the capture structure 506 includes a substantially cylindrical threaded region 534 that is coaxially aligned with an axis of rotation of the shank body 508. The region 534 terminates at an annular seating surface 535. The illustrated capture structure 506 has a maximum radius that is less than a radius associated with the shank thread 510.

The capture structure 506 has a plurality of tool engageable grooves, apertures or the like 536 to enable positive engagement by an appropriately shaped installation tool 538 to thread and drive the shank body 508 into the vertebra 513 as will be discussed in greater detail below. The illustrated shank capture structure 506 includes four evenly spaced tool engageable grooves 536, but it is foreseen that the driving structure may include fewer grooves, an alternative configuration of grooves or other driver receiving structure. An upper end surface 540 of the capture structure 506 opposite the tip 530 is provided with a formation or dome 542 to be positively and interferingly engaged by the insert 524, which in turn is positively engaged by the rod 516 when the assembly 501 is assembled into place. The illustrated dome 542 is radiused, knurled and centered on the upper end surface 540 so as to be coaxial with the remainder of the shank 504. The scoring or knurling of the dome 542 operably frictionally abuts against the insert 524 when the insert 524 is rotated into engagement with the head or receiver 514, as described more fully below, to provide for a selected setting of a desired angle of articulation between the shank body 508 and the head or receiver 514 prior to insertion and locking down of the rod 515. It is foreseen that in certain embodiments, the purpose of the dome 542 is simply to be engaged by the insert 524 that is in turn engaged by the rod 516, pushing the shank 504 in such a manner as to frictionally engage the retaining and articulating structure 520 with the head or receiver 514 as described below. Preferably, the dome 542 is radiused so that the dome 542 engages the insert 524 at approximately the same location regardless of the angle of articulation of the shank body 508 with respect to the head or receiver 514. However, it is foreseen that in certain embodiments shapes other than the dome 542 could be utilized. In the embodiment shown in FIGS. 43-54, the upper end 540 supporting the dome 542 has a hex-shaped profile with side surfaces 543 configured to mate with an assembly or driving tool (not shown).

Referring to FIGS. 43-48, the head or receiver 514 is generally cylindrical in external profile and has a central and axially aligned shank receiving bore 546 ending at an inner and lower neck 547. The neck 547 is radiused to receive the shank capture structure 506 and preferably smaller than a radius of the shank body 508 and thread 510. The bore 546 is also preferably sized larger than the capture structure 506 of the shank 504 to enable the shank 594 to be oriented through a range of angular dispositions relative to the head or receiver 514. The bore 546 may be conically counter-bored or beveled in a region 548 to widen the angular range of the shank 504.

The head or receiver 514 is provided with a U-shaped rod cradle 550 sized to receive the rod 516 therethrough. The illustrated cradle 550 is rounded and radiused at an inner or lower portion or seat 552 to snugly mate with a cylindrical outer surface 554 of the rod 516 and open at an outer end or top 556, with spaced apart side surfaces 558 so as to form upstanding and spaced apart arms 560. The side surfaces 558 have guide and advancement structures 562 formed thereon that are complementary to guide and advancement structures 564 of the closure top 526 (FIG. 54). The illustrated structures 562 and 564 are helically wound flanges or threads that advance the closure top 526 into the head or receiver 514, as the closure top 526 is rotated about a central axis thereof. It is foreseen that the structures 562 and 564 may be interlocking helical flange forms similar to the structures 62 and 252 previously described herein with respect to the assembly 1, V-shaped threads, buttress threads, reverse angle threads, or other types of threads or flange forms. Preferably, the structures 562 and 564 are of such a nature as to resist splaying of the arms 560 when the closure top 526 is advanced into the U-shaped cradle 550.

Furthermore the head or receiver 514 includes an assembly cavity 566 formed therein that opens into the cradle 550. A partially spherical socket or seat 568 defines the assembly cavity 566. The seat 568 is disposed between the arm inner surfaces 558 and the neck 547 defining the shank bore 546 and as illustrated has a radius that is slightly less than a radius of the assembly cavity 566. The seat 568 has a substantially spherical shape and extends upward coaxially through the head or receiver 514 from the neck 547 to the cavity 566. The cavity 566 and the seat 568 will be detailed further below.

Each arm inner surface 558 further includes a recessed portion 570 disposed between the guide and advancement structure 562 and the seat 568. The portion 570 is defined by an upper shoulder 572, a lower shoulder 574 and a wall 576 disposed between the upper and lower shoulders 572, 574. The wall 576 is parallel to an axis of rotation of the head or receiver 514 that is operably coaxial with the shank 504. As will be described in greater detail below, the insert 524 may be operably disposed in the recessed portion 570 and include a setting position wherein the insert 524 abuts against the upper shoulder 572 and presses against the shank capture structure dome 542, allowing for the setting of a desired angle of articulation of the bone screw shank body 508 with respect to the head 514 during surgery, prior to lock down of the rod 516 by the closure top 526. The head or receiver 514 may further include external, closed end grip bores 578 for positive engagement by a holding tool (not shown) to facilitate secure gripping of the head 514 during assembly, installation and/or manipulation of the assembly 501.

The retaining and articulating structure 520, best illustrated in FIGS. 43-48 and 54 is used to retain the capture structure 506 within the head or receiver 514. The retaining and articulating structure 520 is in the form of a ring. The retaining and articulating structure 520 includes a top surface 582, a bottom surface 584, an inner surface 586 having a thread 587 and an outer surface 588. The thread 587 is sized and shaped to mate with the threaded region 534 of the capture structure 506. The retaining and articulating structure 520, similar to a remainder of the assembly 501, is preferably formed of a material such as a spring stainless steel, tantalum, titanium or other resilient implantable material.

The retaining and articulating structure outer surface 588 is frusto-spherical, partially spherical, or a segment of a sphere, with a spherical radius approximately equivalent to the spherical radius of the spherical seat 568 within the head or receiver 514 and smaller than a radius of the cavity 566. As will be described more fully below, the bottom surface 584 seats upon the annular seating surface 535 of the shank capture structure 506 when the retaining and articulating structure 520 is fully installed on the capture structure 506.

The closure top 526 is generally cylindrical in shape and is provided with a break-off head 590 that is connected to the closure top 526 by a weakened area or neck 592 such that the break-off head 590 separates from the closure top 526 at a predetermined torque applied to the break-off head 590 during assembly. The illustrated break-off head 590 has a hexagonal cross section for engagement by a tool (not shown) of a complementary shape. The closure top 526 further includes a central point 594 for abrading and/or penetrating the rod 516 when fully installed on the head 514. Furthermore, the closure top 526 includes a driving formation, such as a hex aperture (not shown) for removal of the closure top, if desired, after the break-off head 590 is broken off.

The insert 524 is best illustrated in FIGS. 43, 47 and 49-54. The insert 524 includes a substantially conical base portion 601 integral with a body portion 604. The base portion 601 extends outwardly from an annular, flat bottom surface 602 to the body portion 604. The body portion 604 is oblong, having a width W' that is smaller than a length L' thereof. The width W' is bounded by two substantially flat surfaces 605. The width W' is slightly smaller than a distance between the inner surfaces of the arms 558 of the head 514. The length L', taken along a center line 606 is slightly smaller than a diameter of the recessed portion 570 measured between the surfaces 576. A U-shaped cradle or channel 607 running parallel to the width W extends through the body portion 604, and is sized and shaped to receive the rod 516 thereon as will be described more fully below. Arms 608 disposed on either side of the cradle 606 each included a top surface 610 that is parallel to the bottom surface 602 and a sloped surface 612, starting at the top surface 610 and sloping downwardly toward the base portion 601. The arms 608 also include rounded, substantially cylindrical side surfaces 614, each having a radius slightly smaller than a radius of the wall 576 that partially defines the recessed portion 570 of the head 514. The sloped surfaces 612 are disposed opposite one another and the top surfaces 610 are disposed opposite one another. The sloped surfaces 612 also slope in opposite directions, each starting at the center line or axis 606 and running outwardly and downwardly away therefrom to provide for a cam action when the insert 524 is placed in the head 514 as shown in FIG. 49, and then rotated, the sloped surfaces 612 engaging the upper shoulder 572 of the recessed portion 570 of the head 514 and thus transforming the circular motion of rotating the insert 524 in the recessed portion 570 of the head 514 into linear motion, pressing the insert 524 against the shank dome 542 as will be described more fully below.

Each arm 608 of the body portion 604 includes a substantially flat bottom surface 616 extending from the conical base portion 601 to the cylindrical surface 614. The base portion 601 further includes a centrally located concave, substantially spherical bottom formation 618 contiguous to the annular bottom surface 602. The spherical bottom formation 618 is sized and shaped to cooperate and engage with the dome 642 of the shank capture structure 606, providing a snug, frictional fit. Apertures 620 extend through the U-shaped cradle 607 and are sized and shaped to cooperate and align with the apertures 536 of the capture structure 506.

Thus, in the illustrated embodiment, four evenly spaced apertures 620 extend through the insert 524 and axially align with the apertures 536 as illustrated in FIGS. 49 and 53, both when the insert 524 is initially placed in the head 514 and when the insert 524 is rotated within the head 514 such that the top surfaces 610 are adjacent the upper shoulder 571. The alignment of the apertures 620 and the apertures 536 as shown in FIG. 53 allow for engagement between the capture structure 506, the insert 524 and the driving tool 538 as will be described more fully below.

A pair of points 622 are disposed in the U-shaped cradle 607 and project therefrom. The points 622 are disposed along the center line 606 and near the surfaces 610 and 612, but could be placed in other areas. The points 622 are sized and shaped to abrade and penetrate the rod 516 as will be described more fully below. One to six or more points could be utilized.

The driver 538 illustrated at FIG. 52 includes a handle (not shown), a drive shaft 626 and an engagement portion 628. The engagement portion 626 includes four prongs 632 extending therefrom sized and shaped to extend through the apertures 620 of the insert 524 and into the apertures 536 in the capture structure 506, thus operably engaging both the bone screw shank 504 and the insert 524 when rotating and driving the shank body 508 into the vertebra 513.

FIGS. 43-47 illustrate the assembly of the bone screw head 514, shank 504 and retaining and articulating structure 520. In FIG. 44, the retaining and articulating structure 520 is inserted into the head 514 through an interior of the U-shaped cradle 550. The retaining and articulating structure 520 is first oriented with a central axis thereof at a right angle to a central axis of the bore 546. Then, the retaining and articulating structure is oriented as illustrated in FIG. 45 with the central axis of the retaining and articulating structure 520 being parallel or coincident with the axis of the bore 546 and the neck 547, by rotating the retaining and articulating structure 520 within the assembly cavity 566. With reference to FIG. 56, the capture structure 506 of the shank 504 is then inserted through the head bore 546 and then rotated with respect to the retaining and articulating structure 520, mating the threaded region 534 with thread 587 disposed on the inner surface 586 of the retaining and articulating structure 520. As illustrated in FIG. 47, when fully seated, the bottom surface 584 of the retaining and articulating structure 520 abuts against the annular seating surface 535 of the capture structure 506.

FIGS. 47 and 48 show the assembly 501 with the retaining and articulating structure 520 lowered from the assembly position and positioned in the spherical seat 568 with the central axis of the shank 504 coaxial with the central axis of the head 514. However, similar to the assembly 1, the relevant discussion of which is incorporated by reference herein, the curved or spherical seat 568 and the curved or spherical outer surface 588 of the retaining and articulating structure 520, allows universal angular positioning of the shank 504 relative to the head 514. The retaining and articulating structure 520, thus performs the functions of preventing the capture structure 506 of the shank 504 from slipping through the neck 547 and, in conjunction with the seat 568, forms a ball joint for relative orientation of the shank 504 and the head 514.

The insert 524 is then loaded into the head 514 as illustrated in FIGS. 47 and 49, with the width dimension W' being oriented as shown with respect to the arms 560 to allow top loading of the insert 524. The insert 524 is lowered into the head 514 until the concave bottom formation 618 is seated on the dome 542.

For driving the bone screw shank body 508 into bone, such as the vertebra 513, the insert 524 is first rotated axially as illustrated in FIGS. 52 and 53, with the sloping surfaces 612 of the insert 524 contacting the upper shoulder 572 defining the head recessed portion 570, thereby pushing the capture structure 506 and attached retaining and articulating structure 520 downwardly against the seat 568. As the insert is rotated approximately 90 degrees until the flat surfaces 610 fully engage the upper shoulder 572, the insert 524 functions as a cam, providing a mechanical linkage that converts rotary motion to linear motion. Frictional engagement between the retaining and articulating structure 520 and the seat 568 sets the bone shank 504 in an angular position with respect to the head 514, but does not lock such into position. Thus, the insert 524 may be used at any time during a procedure to set the shank body 508 at a desired angle with respect to the head 514, but that position is not rigidly fixed until the rod 516 presses down upon the insert 524. When the insert flat surfaces 610 engage the upper shoulder 572, the apertures 620 of the insert 524 are aligned with the apertures 536 of the capture structure 506 and the insert cradle 607 is oriented in a position to receive the oblong support 630 of the driving tool engagement portion 628.

With particular reference to FIG. 52, the assembly 501 is screwed into a bone, such as the vertebra 513, by rotation of the shank 504 using the driving tool 538 that operably drives and rotates the shank 504 by engagement thereof with the apertures 620 of the insert 524 and the apertures 536 of the capture structure 506. The driving tool 538 is inserted into the head 514 of the bone screw with the prongs 632 first inserted into the apertures 620 and then the apertures 536, and then driven and rotated into bone.

Alternatively, the assembly 501 may be driven into bone prior to placement of the insert 524 in the head 514. A hex driving tool (not shown) sized and shaped to mate with the surfaces 543 of the capture structure 506 may be used to rotate and drive the shank body 508 into the vertebra 513. Thereafter, the insert 524 may be placed in the bone screw head 514 as shown in FIG. 47.

Typically at least two and up to a plurality of bone screw assemblies 501 are implanted into vertebrae for use with the rod 516. As described with respect to the assembly 1, and incorporated by reference herein, each vertebra 513 may be pre-drilled to minimize stressing the bone. Although not shown, the assembly 501 may be cannulated in a manner as described with respect to the assembly 1 so that a guide wire or pin may be used as a guide for the placement and angle of the assembly 501. The shank body 508 is then driven into the vertebra 513, by rotation of the driving tool 538.

With reference to FIG. 54, the rod 516 is eventually positioned within the head U-shaped rod cradle 550, and the closure top 526 is then inserted into and advanced between the arms 560. Before rod insertion, it may be desirable to rotate the insert 524 to a position disengaged from the shank domed top 542 as shown in FIG. 47, to allow for a loose angular connection of the shank body 508 with respect to the head 514 until a desired angle of articulation is decided upon. The driving tool 538 may be utilized to rotate the insert 524 by inserting the prongs 632 in the apertures 620. Then, the insert 524 may be rotated to the position shown in FIG. 53, setting, but not locking such desired angular orientation between the shank body 508 and the head 514. In other words, when the insert 5324 is in contact with the upper shoulder 572, the insert 524 presses down on the shank 504, providing sufficient frictional engagement between the retaining and articulating structure 520 and the head seat 568 that the shank 504 resists angular movement. However, it may not be desirable to rotate the insert 524 in order to change the angular orientation of the shank 504 with respect to the head 514. The shank 504 may simply be moved, using some force, to a desired position, which will then be the set position.

With reference to FIG. 54, the rod 516 is seated on the insert 524 and the closure top 526 is initially placed between the arms 560 and rotated using an installation tool (not shown) engaged with surfaces of the break-off head 590 until the guide and advancement structure 564 is fully mated with the head guide and advancement structure 562, with the point 594 penetrating the rod 516 and also the points 622 penetrating the rod 516. The break-off head 590 is then twisted to a preselected torque, for example 90 to 120 inch pounds, until broken off.

If removal of the assembly 501 is necessary, or if it is desired to release the rod 516 at a particular location, disassembly is accomplished by using a tool (not shown) with a driving formation (not shown) located on or in the closure top 526 to rotate and remove the closure top 526 from the head 514. Disassembly of the assembly 501 is accomplished in reverse order to the procedure described previously herein for assembly.

It is to be understood that while certain forms of the present invention have been illustrated and described herein, it is not to be limited to the specific forms or arrangement of parts described and shown.

What is claimed is:

1. A pivotal bone anchor assembly configured for positional locking to a bone of a patient with tooling prior to securing an elongate rod to the bone with a closure, the pivotal bone anchor assembly comprising:
    a bone anchor comprising a capture portion and a body extending distally from the capture portion with an anchor portion configured for fixation to the bone;
    a receiving member having a longitudinal axis, an upper portion configured to receive the elongate rod, and an integral lower portion configured to receive the capture portion, with the bone anchor being configured for pivotal movement with respect to the receiving member upon a positioning of the capture portion in the lower portion in a non-locked configuration; and
    a locking member configured for non-threaded engagement with the receiving member and for vertical displacement along the longitudinal axis into a locked configuration by the tooling, so as to apply a locking force to the capture portion independent of the elongate rod and the closure and thereby lock an angular position of the bone anchor relative to the receiving member,
    wherein the locking member is releasable from the locked configuration by the tooling, so as to remove the locking force on the capture portion and thereby re-establish pivotal movement of the bone anchor with respect to the receiving member, when the elongate rod is positioned in the receiving member.

2. The pivotal bone anchor assembly of claim 1, wherein displacing the locking member into the locked configuration by the tooling further comprises moving the locking member downwardly along the longitudinal axis relative to the receiving member.

3. The pivotal bone anchor assembly of claim 1, wherein releasing the locking member from the locked configuration by the tooling further comprises moving the locking member upwardly along the longitudinal axis relative to the receiving member.

4. The pivotal bone anchor assembly of claim 1, wherein the locking member is configured for the vertical displacement by the tooling when the closure is positioned in the receiving member.

5. The pivotal bone anchor assembly of claim 1, wherein the capture portion is positioned in the lower portion of the receiving member through a lower opening formed in the receiving member.

6. The pivotal bone anchor assembly of claim 1, wherein the locking member engages the capture portion of the bone anchor.

7. The pivotal bone anchor assembly of claim 1, wherein the locking member engages the elongate rod when the elongate rod is positioned in the receiving member in a completely assembled and locked configuration.

8. The pivotal bone anchor assembly of claim 1, wherein the capture portion of the bone anchor is spaced apart from an interior surface of the lower portion of the receiving member when positioned in the receiving member.

9. The pivotal bone anchor assembly of claim 1, wherein the receiving member upper portion further comprises:
    an open channel sized and shaped to receive the elongate rod, and
    a splay-resisting helically wound thread formed into the open channel for engagement with the closure.

10. The pivotal bone anchor assembly of claim 8, further comprising at least one radiused horizontally-elongated upper tool engagement structure formed on a side outer face of the receiving member on either side of the open channel, each upper tool engagement structure being spaced an equal distance below top side surfaces on the receiving member and having downwardly-facing surfaces extending to at least one of a front outer face and a back outer face of the receiving member, the upper tool engagement structures being symmetrically configured about the open channel.

11. A pivotal bone anchor assembly configured for positional locking to a bone of a patient with tooling prior to securing an elongate rod to the bone with a closure, the pivotal bone anchor assembly comprising:

a bone anchor comprising a capture portion and a body extending distally from the capture portion with an anchor portion configured for fixation to the bone;

a receiving member having a longitudinal axis, an upper portion having an open channel configured to receive the elongate rod and the closure and an outer surface with a first tool engagement structure, and an integral lower portion configured to receive the capture portion, with the bone anchor being configured for pivotal movement with respect to the receiving member upon a positioning of the capture portion in the lower portion in a non-locked configuration; and a locking member configured for non-threaded engagement with the receiving member and having an outer surface with a second tool engagement structure spaced below the first tool engagement structure, the locking member being postionable in a locked configuration to apply a locking force to the capture portion prior to the elongate rod and the closure being received in the open channel, so as to lock an angular position of the bone anchor relative to the receiving member, wherein the locking member is movable by the tooling when the tooling is engaged with the second tool engagement structure, so as to release the locking force on the capture portion to reestablish pivotal movement between the receiving member and the bone anchor.

12. The pivotal bone anchor assembly of claim 11, wherein the locking member is configured for vertical displacement along the longitudinal axis of the receiving member by the tooling to release the locking force on the capture portion.

13. The pivotal bone anchor assembly of claim 12, wherein releasing the locking member from the locked configuration by the tooling further comprises moving the locking member upwardly along the longitudinal axis relative to the receiving member.

14. The pivotal bone anchor assembly of claim 11, wherein the locking member is configured for downward displacement along the longitudinal axis relative to the receiving member by the tooling from the non-locked configuration to the locked configuration.

15. The pivotal bone anchor assembly of claim 11, wherein the locking member is vertically displaceable by the tooling when the closure is positioned in the open channel of the receiving member.

16. The pivotal bone anchor assembly of claim 11, wherein the locking member is configured for rotational movement around the longitudinal axis of the receiving member by the tooling to release the locking force on the capture portion.

17. The pivotal bone anchor assembly of claim 11, wherein the locking member further comprises a radiused bottom surface configured to engage a radiused top surface on the capture portion.

18. The pivotal bone anchor assembly of claim 11, wherein the locking member further comprises a central opening.

19. The pivotal bone anchor assembly of claim 11, wherein the capture portion is positioned in the lower portion of the receiving member through a lower opening formed in the receiving member.

20. The pivotal bone anchor assembly of claim 11, further comprising a splay-resisting helically wound thread formed into the open channel of the receiving member for engagement with the closure.

21. The pivotal bone anchor assembly of claim 11, wherein the first tool engagement structure further comprises at least one radiused horizontally-elongated upper tool engagement structure formed on a side outer face of the receiving member on either side of the open channel, each upper tool engagement structure being spaced an equal distance below top side surfaces on the receiving member and having downwardly-facing surfaces extending to at least one of a front outer face and a back outer face of the receiving member, the upper tool engagement structures being symmetrically configured about the open channel.

22. The pivotal bone anchor assembly of claim 11, wherein the second tool engagement structure further comprises at least one horizontally elongated laterally protruding structure formed on each opposite side outer face of the locking member.

* * * * *